US011534359B2

(12) United States Patent
Takahashi et al.

(10) Patent No.: US 11,534,359 B2
(45) Date of Patent: Dec. 27, 2022

(54) ACTUATOR-EQUIPPED KNEE ANKLE FOOT ORTHOSIS

(71) Applicants: SUNCALL CORPORATION, Kyoto (JP); NATIONAL UNIVERSITY CORPORATION KYOTO INSTITUTE OF TECHNOLOGY, Kyoto (JP); KYOTO UNIVERSITY, Kyoto (JP)

(72) Inventors: Rei Takahashi, Kyoto (JP); Yuichi Sawada, Kyoto (JP); Yoshiyuki Higashi, Kyoto (JP); Tadao Tsuboyama, Kyoto (JP); Noriaki Ichihashi, Kyoto (JP); Koji Ohata, Kyoto (JP); Toshikazu Kawaguchi, Daito (JP)

(73) Assignees: Suncall Corporation, Kyoto (JP); National University Corporation Kyoto Institute of Technology, Kyoto (JP); Kyoto University, Kyoto (JP)

( * ) Notice: Subject to any disclaimer, the term of this patent is extended or adjusted under 35 U.S.C. 154(b) by 429 days.

(21) Appl. No.: 16/303,957

(22) PCT Filed: May 19, 2017

(86) PCT No.: PCT/JP2017/018803
§ 371 (c)(1),
(2) Date: Nov. 21, 2018

(87) PCT Pub. No.: WO2017/208851
PCT Pub. Date: Dec. 7, 2017

(65) Prior Publication Data
US 2020/0315899 A1 Oct. 8, 2020

(30) Foreign Application Priority Data
Jun. 1, 2016 (JP) .............................. JP2016-109755

(51) Int. Cl.
*A61H 3/00* (2006.01)
*A61F 5/01* (2006.01)

(52) U.S. Cl.
CPC .............. *A61H 3/00* (2013.01); *A61F 5/0111* (2013.01); *A61F 2005/0155* (2013.01);
(Continued)

(58) Field of Classification Search
CPC .. A61F 5/01; A61F 5/0111; A61F 2005/0155; A61H 2201/164;
(Continued)

(56) References Cited

U.S. PATENT DOCUMENTS 10,556,335 B2 * 2/2020 Roh ....................... B25J 9/0006
2007/0038268 A1 * 2/2007 Weinberg ................. A61H 3/00
607/62
(Continued)

FOREIGN PATENT DOCUMENTS

JP 5724312 4/2005
JP 2005-211328 8/2005
(Continued)

OTHER PUBLICATIONS

International Search Report of PCT/JP2017/018803 dated Aug. 15, 2017.
Notification Concerning Transmittal of International Preliminary Report on Patentability of PCT/JP2017/018803 dated Dec. 13, 2018.

*Primary Examiner* — Valerie L Woodward
*Assistant Examiner* — Paige Kathleen Bugg
(74) *Attorney, Agent, or Firm* — Sterne, Kessler, Goldstein & Fox P.L.L.C.

(57) ABSTRACT

The present invention provides an actuator-equipped knee ankle foot orthosis in which a control device calculates a thigh phase angle based on an angle-related signal detected by a thigh orientation detecting means at one sampling point, applies the thigh phase angle at that sampling point to an
(Continued)

assisting force control data, which is stored in the control device in advance and indicates the relationship between the thigh phase angle and a size of the assisting force to be imparted to a lower leg-side brace, to obtain the size of the assisting force to be imparted to the lower leg-side brace at that sampling point, and executes operational control for an actuator unit such that the assisting force having the size is output.

4 Claims, 13 Drawing Sheets

(52) U.S. Cl.
CPC .. *A61H 2003/007* (2013.01); *A61H 2201/164* (2013.01); *A61H 2201/165* (2013.01); *A61H 2201/5069* (2013.01); *A61H 2201/5071* (2013.01); *A61H 2201/5079* (2013.01); *A61H 2205/102* (2013.01); *A61H 2205/106* (2013.01)

(58) Field of Classification Search
CPC ...... A61H 2201/165; A61H 2201/5069; A61H 2201/5071; A61H 2201/5079; A61H 2205/102; A61H 2205/106; B25J 9/0006; B25J 9/104; B25J 9/1694
USPC .......................................................... 601/5
See application file for complete search history.

(56) References Cited

U.S. PATENT DOCUMENTS

| | | | | |
|---|---|---|---|---|
| 2011/0033835 | A1* | 2/2011 | Endo | G09B 19/0038 434/365 |
| 2012/0259431 | A1* | 10/2012 | Han | A61H 1/024 623/24 |
| 2014/0081420 | A1* | 3/2014 | Herr | A61F 2/6607 623/25 |
| 2015/0190923 | A1* | 7/2015 | Seo | A61H 1/0266 602/16 |
| 2015/0196449 | A1* | 7/2015 | Ahn | A61H 1/024 623/27 |
| 2016/0338897 | A1* | 11/2016 | Takenaka | A61H 3/00 |
| 2017/0049659 | A1* | 2/2017 | Farris | A61H 1/0244 |
| 2019/0070059 | A1* | 3/2019 | Dalley | A61B 5/1117 |

FOREIGN PATENT DOCUMENTS

| | | |
|---|---|---|
| JP | 5386253 | 10/2013 |
| JP | 2014-184047 | 10/2014 |
| JP | 2015-527167 | 9/2015 |
| JP | 5799608 | 9/2015 |
| JP | 2016-002408 | 1/2016 |

* cited by examiner

ACTUATOR-EQUIPPED KNEE ANKLE FOOT ORTHOSIS

FIELD OF THE INVENTION

The present invention relates to a knee ankle foot orthosis equipped with an actuator.

BACKGROUND ART

Knee ankle foot orthoses for supporting a knee joint are utilized as gait assistance or rehabilitation devices for people with leg disability or people with paralysis due to a stroke or the like, and actuator-equipped knee ankle foot orthoses are also proposed that are equipped with an actuator unit including a driver such as an electric motor for assisting movement of a leg (see Patent Literatures 1 to 3 below).

Specifically, conventional actuator-equipped knee ankle foot orthoses include a thigh-side brace to be attached to a user's thigh, a lower leg-side brace to be attached to the user's lower leg and connected to the thigh-side brace so as to be rotatable around the user's knee joint, an actuator attached to the thigh-side brace and capable of imparting an assisting force around the knee joint to the lower leg-side brace, a lower leg angle sensor for detecting the angle of rotation of the lower leg around the knee joint relative to the thigh, and a control device for managing operational control for the actuator, and are configured such that the control device executes operational control for the actuator based on a detection signal from the lower leg angle sensor.

That is, the above conventional actuator-equipped knee ankle foot orthoses detect movement of the lower leg (the angle of the lower leg around the knee joint relative to the thigh), which is a control target site to which an assisting force is to be imparted by the actuator, by means of the lower leg angle sensor, and perform operational control for the actuator such that assisting force having a size and a direction calculated based on movement of the lower leg is imparted to the lower leg.

However, in the case of paralysis due to a stroke or the like, although gait motion of the thigh (forward and backward swing motion of the thigh around the hip joint) can be performed relatively normally, gait motion of the lower leg (forward and backward swing motion of the lower leg around the knee joint) often cannot be performed normally.

In such a case, since the conventional actuator-equipped knee ankle foot orthoses perform operational control for the actuator based on movement of the lower leg that is incapable of normal gait motion, there is a possibility that suitable gait assisting force cannot be provided.

Meanwhile, a gait assisting device is proposed that includes an imparting unit for imparting assisting force, a control unit for performing operational control for the imparting unit, a detection unit for detecting at least one of a hip joint angle and a hip joint angular velocity, and a calculation unit for calculating the phase angle of the thigh based on a detection result of the detection unit, and that is configured such that the control unit performs operational control for the imparting unit based on the phase angle (see Patent Literature 4 below).

However, the gait assisting device of Patent Literature 4 also detects movement of a control target site to which assisting force is to be imparted and performs operational control for the imparting unit that imparts assisting force to the thigh, which is the control target site, based on a detection result, and is thus based on the same technical idea as the actuator-equipped knee ankle foot orthoses described in Patent Literatures 1 to 3.

PRIOR ART DOCUMENT

Patent Literature

Patent Literature 1: JP 5724312B
Patent Literature 2: JP 5799608B
Patent Literature 3: JP 5386253B
Patent Literature 4: JP 2016-002408A

DISCLOSURE OF THE INVENTION

The present invention has been conceived in view of such conventional art, and an object of the present invention is to provide an actuator-equipped knee ankle foot orthosis including an actuator capable of imparting gait assisting force around a knee joint to a lower leg, the actuator-equipped knee ankle foot orthosis being capable of imparting appropriate gait assisting force to the lower leg according to a gait state during a gait cycle even for a user having difficulty in performing normal gait motion of the lower leg.

In order to achieve the object, a first aspect of the present invention provides an actuator-equipped knee ankle foot orthosis including a thigh-side brace to be attached to the user's thigh; a lower leg-side brace to be attached to the user's lower leg, the lower leg-side brace being connected to the thigh-side brace so as to be rotatable around the user's knee joint; an actuator unit attached to the thigh-side brace and capable of imparting assisting force around the knee joint to the lower leg-side brace; a thigh orientation detecting means capable of detecting an angle-related signal concerning a hip joint angle that is a forward and backward swing angle of the user's thigh; and a control device managing operational control for the actuator unit, wherein the control device calculates a thigh phase angle at one sampling point based on the angle-related signal at that sampling point, applies the thigh phase angle at that sampling point to an assisting force control data, which is stored in the control device in advance and indicates the relationship between the thigh phase angle and a size of the assisting force to be imparted to the lower leg-side brace, to obtain the size of the assisting force to be imparted to the lower leg-side brace at that sampling point, and executes operational control for the actuator unit such that the assisting force having the size is output.

The actuator-equipped knee ankle foot orthosis according to the first aspect of the present invention makes it possible to impart an appropriate gait assisting force to the user's lower leg in response to the gait state in the gait cycle even for a user having difficulty in performing normal gait motion of the lower leg, since the control device is configured to calculate a thigh phase angle based on the angle-related signal concerning the hip joint angle that is detected by the thigh orientation detecting means, apply the thigh phase angle to the assisting force control data, which is stored in the control device in advance and indicates the relationship between the thigh phase angle and the size of the assisting force to be imparted to the lower leg-side brace, to obtain the size of the assisting force to be imparted to the lower leg-side brace at this sampling point, and execute operational control for the actuator unit such that the assisting force having the size is output.

In one embodiment, the thigh orientation detecting means includes a triaxial angular velocity sensor detecting an angular velocity of the user's thigh.

In this case, the control device may calculate the hip joint angle based on angular velocity data from the angular velocity sensor, and calculate the thigh phase angle based on the hip joint angle and a hip joint angular velocity obtained by differentiating the hip joint angle.

In another embodiment, the thigh orientation detecting means includes a triaxial angular velocity sensor detecting an angular velocity of the user's thigh and a triaxial acceleration sensor detecting an acceleration of the user's thigh.

In this case, the control device may calculate a combined Eulerian angle by combining a high-frequency component of a first Eulerian angle calculated based on angular velocity data from the triaxial angular velocity sensor and a low-frequency component of a second Eulerian angle calculated based on acceleration data from the triaxial acceleration sensor, and calculate the thigh phase angle based on a hip joint angle calculated from the combined Eulerian angle and a hip joint angular velocity calculated from the hip joint angle.

Preferably, the control device is configured to plot the hip joint angle and the hip joint angular velocity that has been used when calculating the thigh phase angle to obtain a trajectory diagram that indicates the cyclic motion of the thigh for each gait cycle.

Preferably, the control device is configured to inhibit an operation of the actuator unit in a case where a length of a vector defined by the hip joint angle and the hip joint angular velocity that has been used when calculating the thigh phase angle is less than a predetermined threshold value.

Preferably, the actuator-equipped knee ankle foot orthosis according to the present invention may include a high-pass filter that extracts the high-frequency component of the hip joint angle.

In this case, the control device is configured to differentiate the high-frequency component of the hip joint angle extracted by the high-pass filter to obtain the hip joint angular velocity.

The assisting force control data may include a first torque pattern for preventing knee bending by rotating the lower leg-side brace in the knee extending direction around the knee joint in a heel contact phase that includes a heel contact time point when the user's heel contacts the ground in front of the user's body axis, a second torque pattern for preventing knee bending by rotating the lower leg-side brace in the knee extending direction around the knee joint in a stance phase when the user's heel-contacted leg after heel contact is relatively moved backward while being in contact with the ground, a third torque pattern for assisting the raising of the leg by rotating the lower leg-side brace around the knee joint in the knee bending direction in an initial stage of a swing phase wherein the user's leg contacting the ground since the end of the stance phase is raised and relatively moved forward, and a fourth torque pattern for rotating the lower leg-side brace around the knee joint in the knee extending direction in a later stage of the swing phase.

In order to achieve the object, a second aspect of the present invention provides an actuator-equipped knee ankle foot orthosis including a thigh-side brace to be attached to the user's thigh; a lower leg-side brace to be attached to the user's lower leg, the lower leg-side brace being connected to the thigh-side brace so as to be rotatable around the user's knee joint; an actuator unit attached to the thigh-side brace and capable of imparting assisting force around the knee joint to the lower leg-side brace; a thigh orientation detecting means capable of detecting an angle-related signal concerning a hip joint angle that is a forward and backward swing angle of the user's thigh; and a control device managing operational control for the actuator unit, wherein the control device calculates a thigh phase angle at one sampling point based on the angle-related signal at that sampling point, converts the thigh phase angle into a heel contact phase angle for which heel contact is used as a control reference timing, applies the heel contact phase angle at that sampling point to an assisting force control data, which is stored in the control device in advance and indicates the relationship between the thigh phase angle and a size of the assisting force to be imparted to the lower leg-side brace, to obtain the size of the assisting force to be imparted to the lower leg-side brace at that sampling point, and executes operational control for the actuator unit such that the assisting force having the size is output.

The actuator-equipped knee ankle foot orthosis according to the second aspect of the present invention makes it also possible to impart an appropriate gait assisting force to the user's lower leg in response to the gait state in the gait cycle even for a user having difficulty in performing normal gait motion of the lower leg.

If the hip joint angular velocity when the user's thigh swings forward and backward in reference to the user's body axis is referred to as positive and negative, respectively, the control device may recognize as the heel contact timing the time point at which the calculated hip joint angular velocity advances a predetermined phase angle from the timing at which the calculated hip joint angular velocity reaches zero from a positive value.

The actuator-equipped knee ankle foot orthosis according to the present invention may include a heel contact detecting means for detecting heel contact.

In this case, the control device may recognize a timing detected by the heel contact detecting means as the heel contact time point.

EMBODIMENT FOR CARRYING OUT THE INVENTION

Below, one embodiment of the actuator-equipped knee ankle foot orthosis according to the present invention will now be described with reference to the attached drawings.

Figure 1:
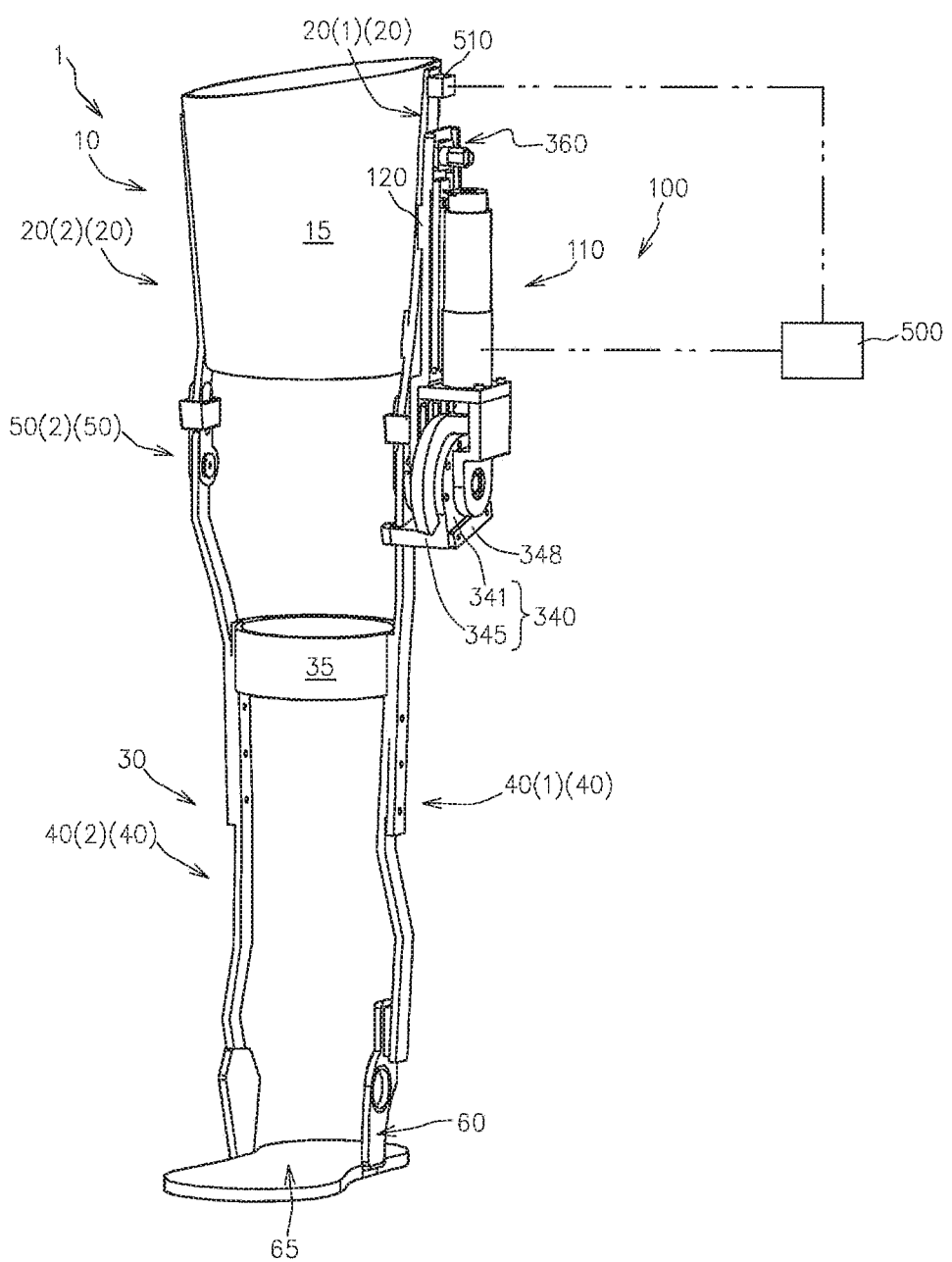
FIG. 1 is a perspective view of a knee ankle foot orthosis according to one embodiment of the present invention.
Figure 2:
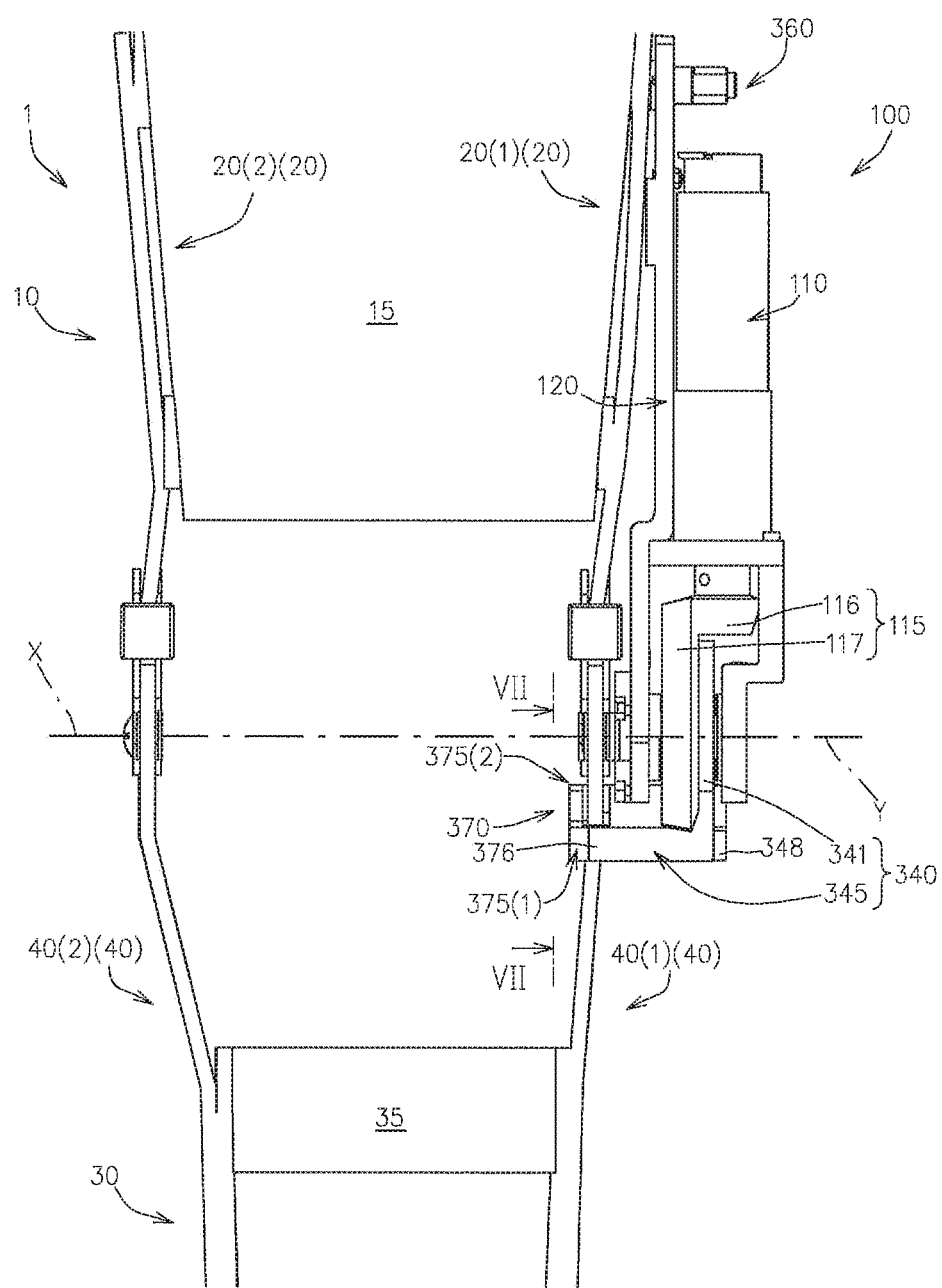
FIG. 2 is a partial front view of the knee ankle foot orthosis.

FIGS. 1 and 2 respectively show a perspective view and a partial front view of a knee ankle foot orthosis 1 according to the present embodiment.

Figure 3:
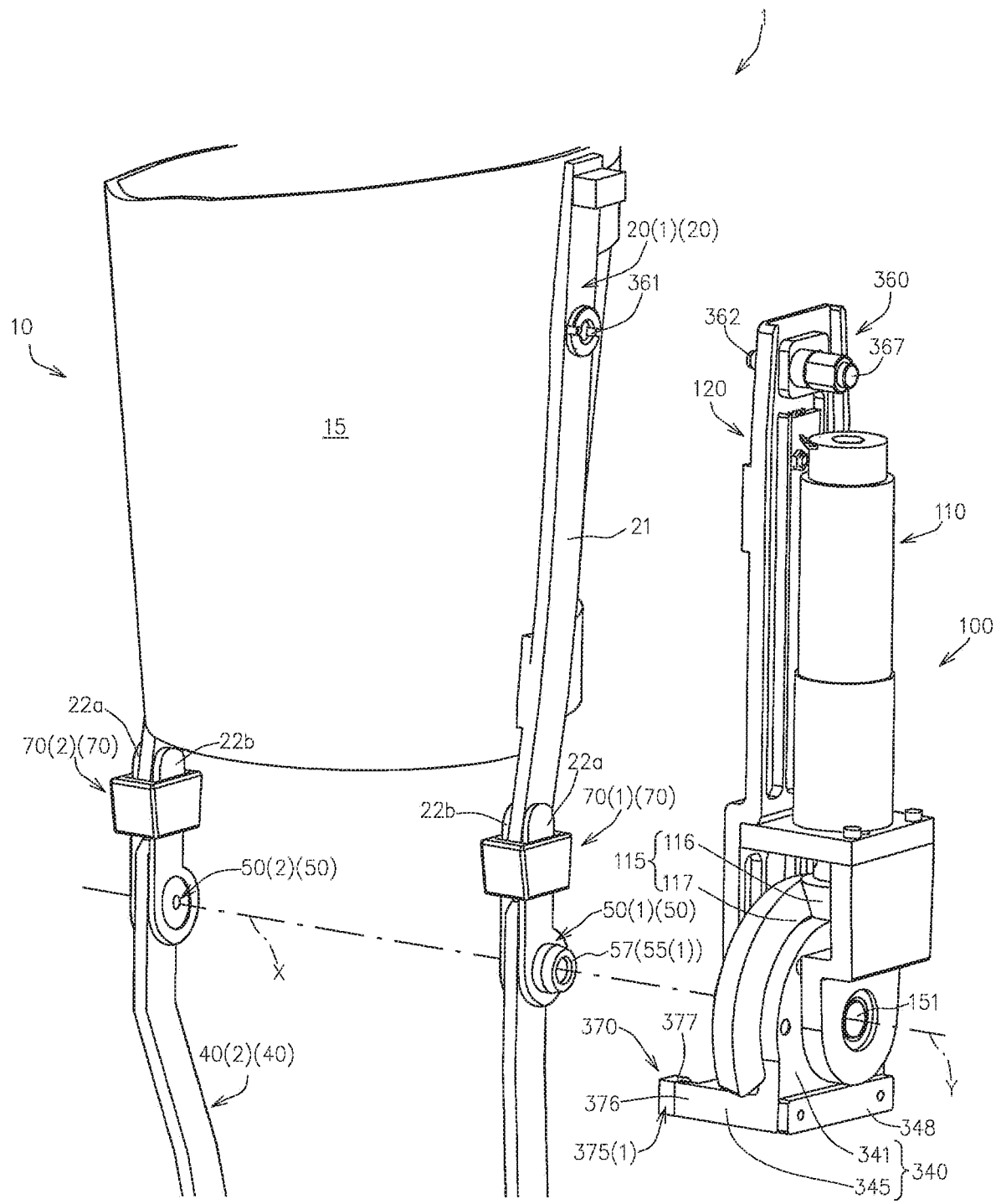
FIG. 3 is a partial exploded perspective view as viewed from the outer side in the width direction of a user of the knee ankle foot orthosis.
Figure 4:
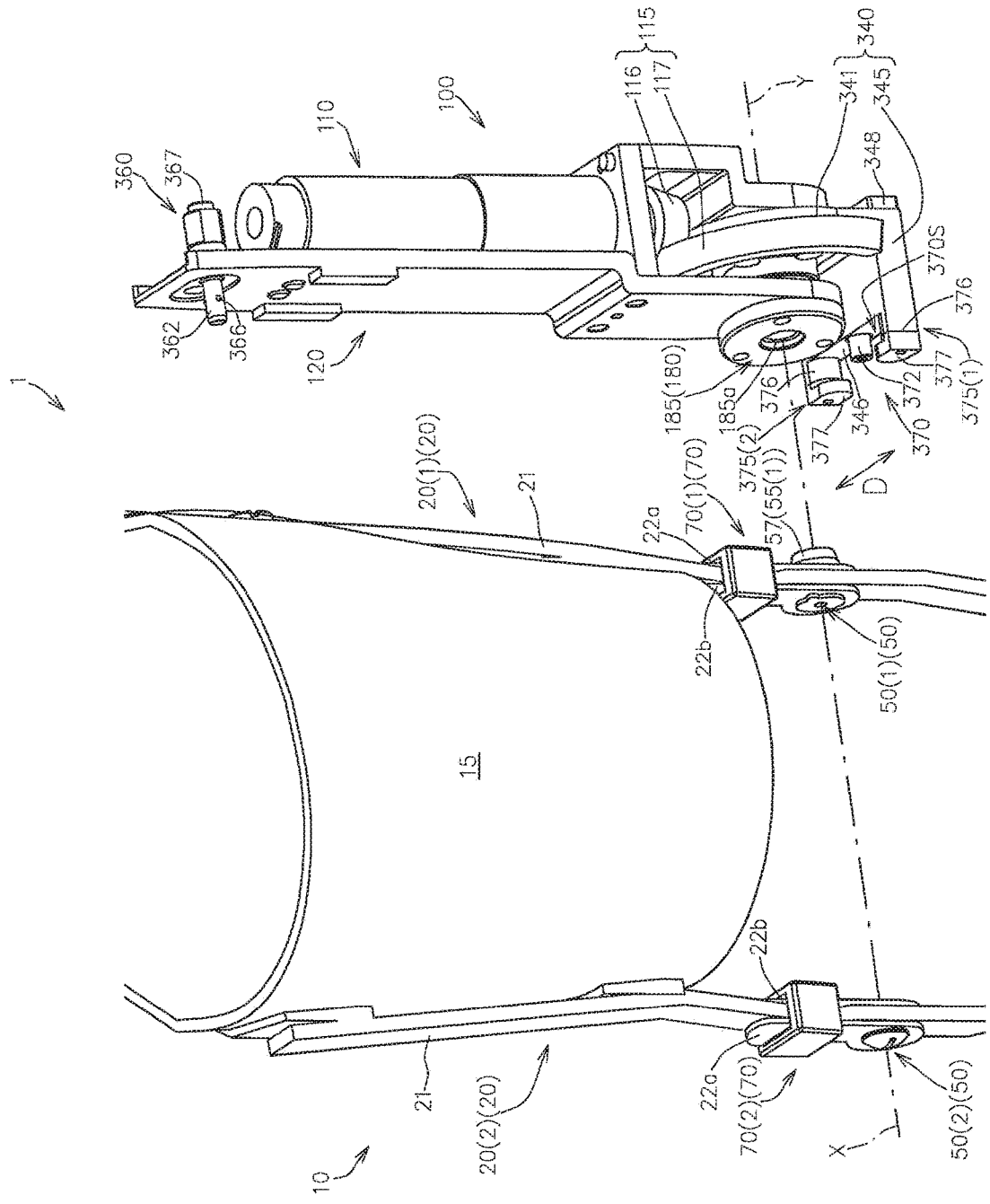
FIG. 4 is a partial exploded perspective views as viewed from the inner side in the width direction of a user of the knee ankle foot orthosis.

FIGS. 3 and 4 respectively show partial exploded perspective views as viewed from the outer side and the inner side in the width direction of a user of the knee ankle foot orthosis 1.

The knee ankle foot orthosis 1 is a device to be worn by a person with leg disability or a user with hemiplegia due to a stroke or the like for gait assistance or for rehabilitation, and is configured to be capable of imparting gait assisting force to the user's lower leg by a provided actuator unit 100.

Specifically, as shown in FIGS. 1 to 4, the knee ankle foot orthosis 1 includes a thigh-side brace 10 to be attached to the user's thigh, a lower leg-side brace 30 to be attached to the user's lower leg, and an actuator unit 100 attached to the thigh-side brace 10 and capable of imparting assisting force around a knee joint to the lower leg-side brace 30.

In the present embodiment, the thigh-side brace 10 has a thigh attachment 15 to be attached to the user's thigh and a thigh frame 20 connected to the thigh attachment 15.

The thigh attachment 15 may take various forms as long as it can be attached to the user's thigh.

In the present embodiment, as shown in FIG. 1, the thigh attachment 15 is in a cylindrical form having an attachment hole with a size such that the user's thigh can be inserted and the thigh attachment fits the thigh.

As shown in FIGS. 1 to 4, the thigh frame 20 has a first thigh frame 20(1) vertically extending along the user's thigh on the outer side in the width direction of the user.

In the present embodiment, as shown in FIGS. 1 to 4, the thigh frame 20 further has a second thigh frame 20(2) vertically extending along the user's thigh on the inner side in the width direction of the user so as to be opposed to the first thigh frame 20(1) with the user's thigh inserted in the thigh attachment 10 in-between.

In the present embodiment, the lower leg-side brace 30 has a lower leg attachment 35 to be attached to the user's lower leg and a lower leg frame 40 connected to the lower leg attachment 35.

The lower leg attachment 35 may take various forms as long as it can be attached to the user's lower leg.

In the present embodiment, as shown in FIG. 1, the lower leg attachment 35 is in a cylindrical form having an attachment hole with a size such that the user's lower leg can be inserted and the lower leg attachment fits the lower leg.

As shown in FIGS. 1 to 4, the lower leg frame 40 has a first lower leg frame 40(1) vertically extending along the user's lower leg on the outer side in the width direction of the user.

In the present embodiment, as shown in FIGS. 1 to 4, the lower leg frame 40 further has a second lower leg frame 40(2) vertically extending along the user's lower leg on the inner side in the width direction of the user so as to be opposed to the first lower leg frame 40(1) with the user's lower leg inserted in the lower leg attachment 30 in-between.

In the present embodiment, the lower leg-side brace 30 further has a foot attachment 65 on which the user places a foot, and a foot frame 60 supporting the foot attachment 65 and connected to the lower leg frame 40.

The lower leg-side brace 30 is connected to the thigh-side brace 10 so as to be rotatable around the user's knee joint.

That is, the lower leg frame 40 is connected to the thigh frame 20 so as to be rotatable around a swing axis X of the user's knee joint.

As described above, in the present embodiment, the thigh frame 20 has the first and second thigh frames 20(1), 20(2), and the lower leg frame 40 has the first and second lower leg frames 40(1), 40(2).

Accordingly, the first lower leg frame 40(1) is connected to the first thigh frame 20(1) so as to be rotatable around the swing axis X, and the second lower leg frame 40(2) is connected to the second thigh frame 20(2) so as to be rotatable around the swing axis X.

Figure 5:
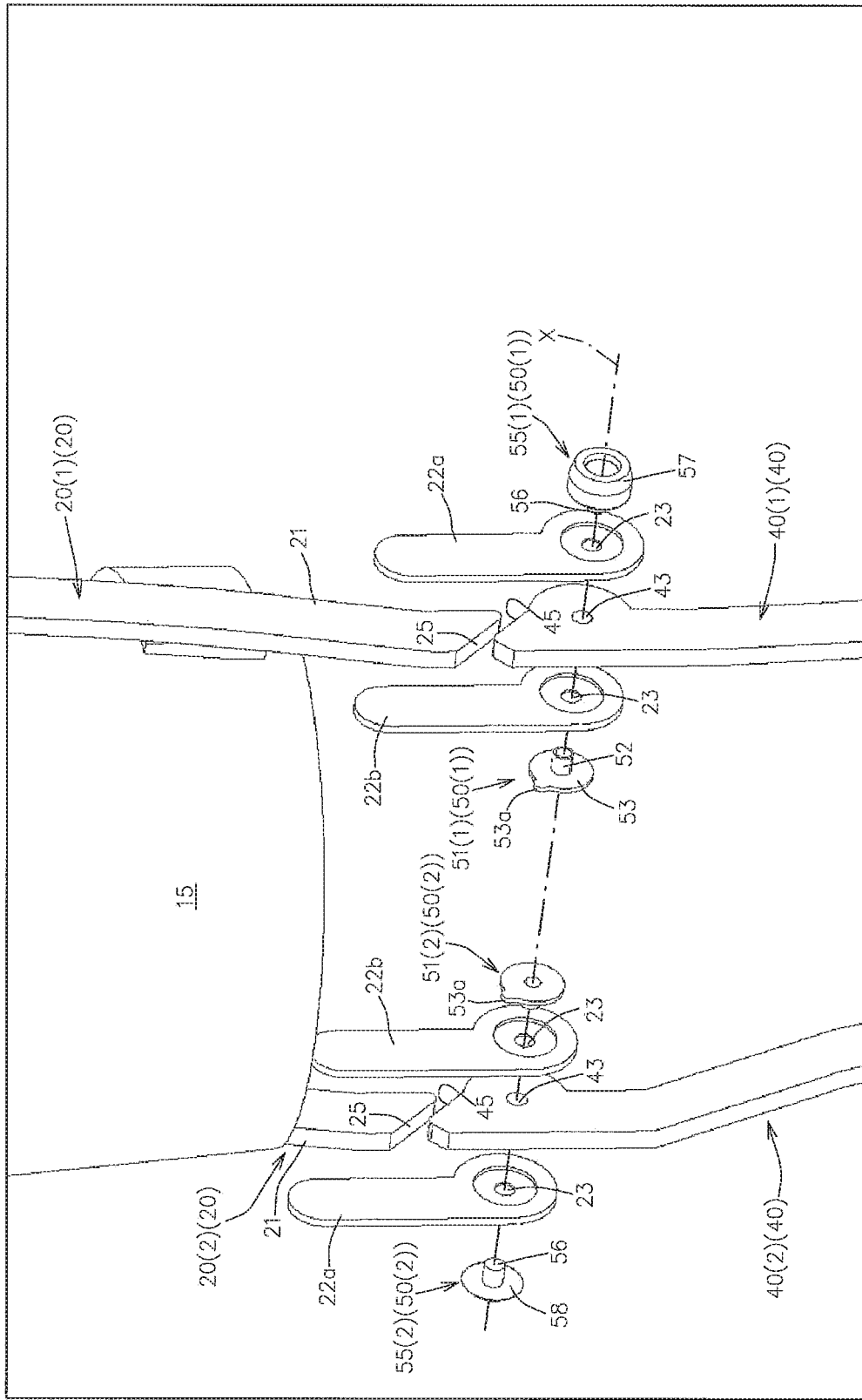
FIG. 5 is an exploded perspective view of a thigh frame and a lower leg frame of the knee ankle foot orthosis.

FIG. 5 shows an exploded perspective view of the thigh frame 20 and the lower leg frame 40.

As shown in FIG. 5, the thigh frame 20 has a vertically extending thigh frame main body 21 and a pair of connecting pieces 22a, 22b fixed to the thigh frame main body 21 by pinning, welding, or the like so as to sandwich a lower end part of the thigh frame main body 21.

The pair of connecting pieces 22a, 22b consist of an outer connecting piece 22a positioned on the side farther from the user's leg than the thigh frame main body 21 is, and an inner connecting piece 22b positioned on the side closer to the user's leg than the thigh frame main body 21 is.

Being interposed between the pair of connecting pieces 22a, 22b, the lower leg frame 40 is connected to the pair of connecting pieces 22a, 22b so as to be rotatable around the swing axis X.

Specifically, attachment holes 23, 43 in the user width direction are formed coaxially with the swing axis X in the pair of connecting pieces 22a, 22b and in the upper part of the lower leg frame 40.

The first thigh frame 20(1) and the first lower leg frame 40(1), which are positioned on the side where the actuator unit 100 is to be provided (on the outer side in the user width direction than the corresponding leg of the user is), are connected via a first rotational connector 50(1) so as to be rotatable around the swing axis X.

The first rotational connector 50(1) has a first internally threaded member 51(1) and a first externally threaded member 55(1) to be separably connected to each other in the attachment holes 23, 43.

The first internally threaded member 51(1) has a cylindrical part 52 to be inserted into the attachment hole 23 from the inner connecting piece 22b side and a flange part 53 extending radially outward from the cylindrical part 52 in a place closer to the user's leg than the attachment hole 23 is, and the cylindrical part 52 has a threaded hole that is open toward the free end side.

The first externally threaded member 55(1) has a cylindrical part 56 to be inserted into the attachment hole 23 from the outer connecting piece 22a side and an engagement projection 57 extending from the cylindrical part 56 in a place farther from the user's leg than the attachment hole 23 is.

The cylindrical part 56 of the first externally threaded member 55(1) has an external thread to be screwed into the threaded hole of the first internally threaded member 51(1) in the attachment holes 23, 43.

By screwing the external thread formed on the first externally threaded member 55(1) into the internal thread of the first internally threaded member 51(1) in the attachment holes 23, 43, the first lower leg frame 40(1) is connected to the first thigh frame 20(1) so as to be capable of swinging.

The second thigh frame 20(2) and the second lower leg frame 40(2), which are positioned on the inner side in the user width direction than the corresponding leg of the user is, are connected via a second rotational connector 50(2) so as to be rotatable around the swing axis X.

The second rotational connector 50(2) has a second internally threaded member 51(2) and a second externally threaded member 55(2) to be separably connected to each other in the attachment holes 23, 43.

The second internally threaded member 51(2) has the same configuration as the first internally threaded member 51(1).

The second externally threaded member 55(2) has the cylindrical part 56 to be inserted into the attachment hole 23 from the outer connecting piece 22a side and the flange part 58 extending radially outward from the cylindrical part 56 on the inner side in the user width direction than the attachment hole 23 is.

The cylindrical part 56 of the second externally threaded member 55(2) has an external thread to be screwed into the threaded hole of the second internally threaded member 51(2) in the attachment holes 23, 43.

By screwing the external thread formed on the second externally threaded member 55(2) into the internal thread of the second internally threaded member 51(2) in the attachment holes 23, 43, the second lower leg frame 40(2) is connected to the second thigh frame 20(2) so as to be capable of swinging.

Reference number 53a in FIG. 5 is a radially outward projection provided on the flange part 53 and engages with a depression formed in the inner connecting piece 22b, and thereby the internally threaded member 51 is retained so as to be incapable of relative rotation around the axis relative to the inner connecting piece 22b (i.e., the thigh frame 20).

In the present embodiment, the knee ankle foot orthosis 1 further has, as shown in FIGS. 1 to 4, a locking member 70 for inhibiting the rotation of the lower leg frame 40 around the swing axis X relative to the thigh frame 20.

The locking member 70 is configured to be capable of attaining a locked state (the state shown in FIGS. 1 to 4) where the thigh frame 20 and the lower leg frame 40 are surrounded by the locking member 70 to connect both frames 20, 40 and prevent the lower leg frame 40 from being relatively rotated around the swing axis X relative to the thigh frame 20, and a cancelled state where connection between the thigh frame 20 and the lower leg frame 40 is cancelled to permit the lower leg frame 40 to be relatively rotated around the swing axis X relative to the thigh frame 20.

In the present embodiment, the locking member 70 has a first locking member 70(1) positioned on the outer side in the user width direction and acting on the first thigh frame 20(1) and the first lower leg frame 40(1), and a second locking member 70(2) positioned on the inner side in the user width direction and acting on the second thigh frame 20(2) and the second lower leg frame 40(2).

In the present embodiment, as shown in FIG. 5, an upper-end surface 45 of the lower leg frame 40 (the end surface facing the thigh frame 20) is a sloped surface such that the radial distance from the swing axis X increases from one side toward the other side around the swing axis X, and a lower-end surface 25 of the thigh frame 20 (the end surface facing the lower leg frame 40) is a sloped surface corresponding to the upper-end surface 45 of the lower leg frame 40.

Due to this configuration, the lower leg frame 40 is permitted to rotate only toward one side around the swing axis X relative to the thigh frame 20 (in the direction in which the user's lower leg is bent relative to the thigh) and permitted to rotate toward the other side such that the lower leg is extended relative to the thigh but not rotate any further.

Figure 6:
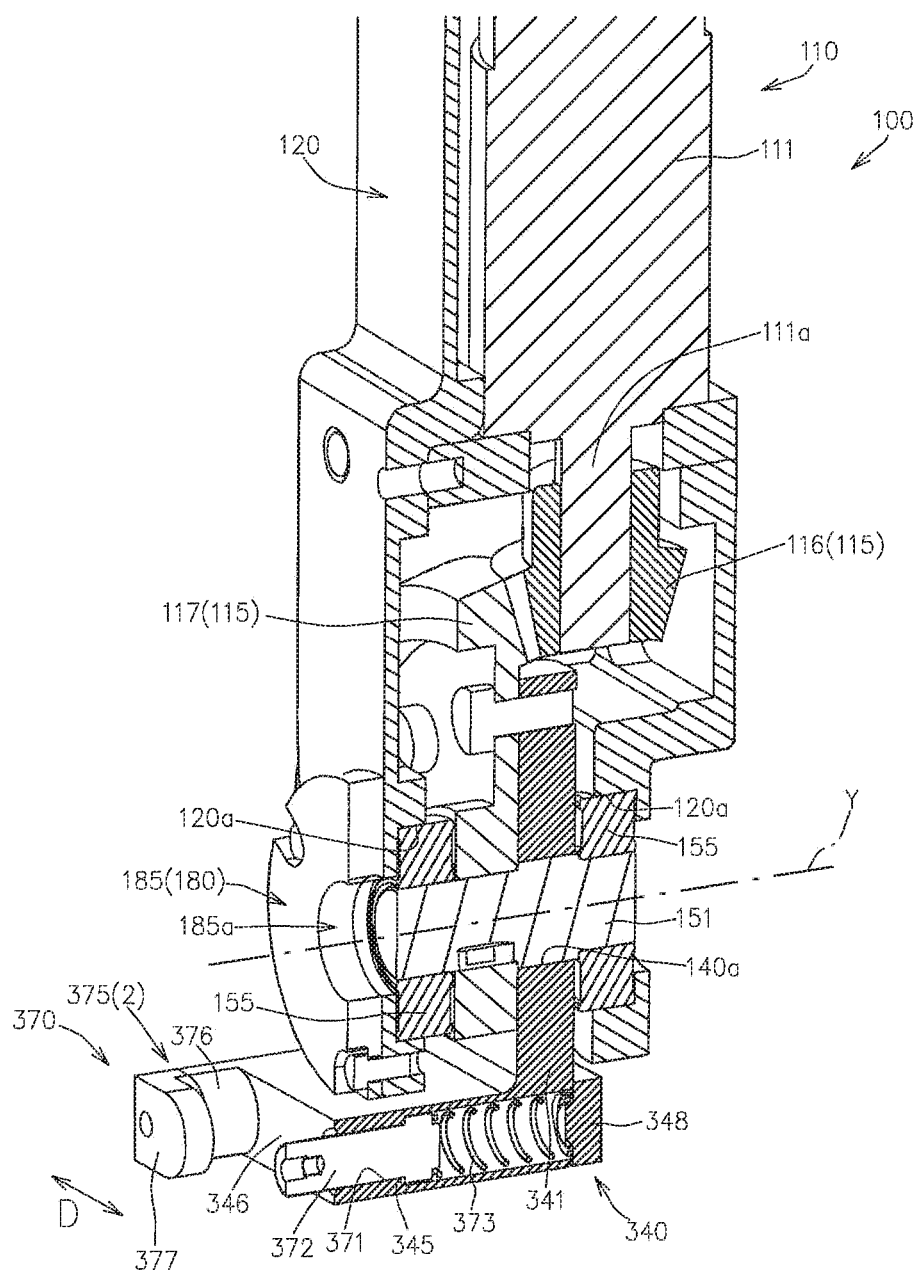
FIG. 6 is a partial longitudinal cross-sectional view of an actuator unit of the knee ankle foot orthosis.

FIG. 6 is a partial longitudinal cross-sectional view of the actuator unit 100. As shown in FIGS. 1 to 4 and 6, the actuator unit 100 includes an upper frame 120, a lower frame 340 connected to the upper frame 120 so as to be rotatable around a pivot axis Y, a driver 110 such as an electric motor for producing driving force for rotating the lower frame 340 around the pivot axis Y, an upper connecting body 360 connecting the upper frame 340 to the thigh frame 20, a rotation center connecting body 180 for positioning the pivot axis Y coaxially with the swing axis X, and a lower connecting body 370.

The upper frame 120 and the lower frame 340 are respectively provided with an upper frame attachment hole 120a and a lower frame attachment hole 140a disposed coaxially with the pivot axis Y.

A rotational connecting shaft 151 is fixed to the lower frame attachment hole 140a, the rotational connecting shaft 151 is supported by the upper frame attachment hole 120a via bearing members 155 so as to be axially rotatable, and thereby the lower frame 340 is connected to the upper frame 120 so as to be rotatable around the pivot axis Y.

The driver 110 has a driving source 111 such as an electric motor, and a transmission mechanism 115 for transmitting driving force produced by the driving source 111 to the lower frame 340.

The driving source 111 is fixed to the outer surface of the upper frame 120.

In the present embodiment, as shown in FIG. 6, the driving source 111 is fixed to the outer surface of the upper frame 120, with an output shaft 111a extending downward.

In the present embodiment, as shown in FIG. 6, the transmission mechanism 115 includes a drive-side bevel gear 116 supported by the output shaft 111a so as to be incapable of relative rotation, and a driven-side bevel gear 117 that is connected to the lower frame 340 so as to be rotated integrally with the lower frame 340 around the pivot axis Y and that is meshed with the drive-side bevel gear 116.

The actuator unit 100 can have a sensor (not shown) for detecting the angle of axial rotation of the rotational connecting shaft 151, and can recognize the swing angle of the lower frame 340 around the pivot axis Y by detecting the angle of axial rotation of the rotational connecting shaft 151 with the sensor.

As shown in FIGS. 3 and 4, the upper connecting body 360 has an engagement hole 361 provided in the first thigh frame 20(1) so as to be parallel to the pivot axis Y and open outward in the user width direction (in the direction of the upper frame 120), and an engagement pin 362 provided on the upper frame 120 so as to be capable of engagement with the engagement hole 361.

In the present embodiment, the upper connecting body 360 is provided with a locking mechanism.

As shown in FIG. 4, the locking mechanism has a projection 366 capable of radially advancing and retreating from the outer surface of the engagement pin 362 and capable of reaching an engagement position where the projection projects radially outward from the outer surface of the engagement pin and a cancelling position where the projection is retreated in the engagement pin, a biasing member (not shown) for biasing the projection 366 toward the engagement position, a depression (not shown) provided in the engagement hole such that the engagement pin 362 inserted in the engagement hole 361 is engaged with the projection 366, and a cancellation operation part 367 for pressing the projection 366 to a cancellation position against the biasing force of the biasing member in response to manual operation from outside.

As shown in FIGS. 4 and 6, the rotation center connecting body 180 has an orthosis-side rotation center connecting member provided on the first thigh frame 20(1) or the first lower leg frame 40(1) so as to be positioned coaxially with the swing axis X, and an actuator-side rotation center connecting member 185 provided on the upper frame 120 or the lower frame 340 so as to be positioned coaxially with the pivot axis Y.

In the present embodiment, the engagement projection 57 of the first rotational connector 50(1) acts as the orthosis-side rotation center connecting member.

The actuator-side rotation center connecting member 185 has an actuator-side depression/projection engagement part 185a capable of being removably depression/projection-engaged with the orthosis-side rotation center connecting member (the engagement projection 57 in the present embodiment).

In the present embodiment, as shown in FIG. 6, the upper frame 120 has an engagement depression into which the orthosis-side rotation center connecting member (the engagement projection 57 in the present embodiment) is to be inserted so as to be removable and axially rotatable, and the engagement depression acts as the actuator-side depression/projection engagement part 185a.

As shown in FIGS. 3, 4, and 6, the lower connecting body 370 connects the lower frame 340 to the first lower leg frame 40(1) such that the first lower leg frame 40(1) is rotated around the swing axis X relative to the first thigh frame 20(1) in response to the rotational movement of the lower frame 340 around the pivot axis Y relative to the upper frame 120.

Specifically, as shown in FIG. 6, the lower frame 340 has a proximal end part 341 connected to the upper frame 120 via the rotational connecting shaft 151 so as to be rotatable around the pivot axis Y, and a distal end part 345 extending from the proximal end part 341 toward the first lower leg frame 40(1).

As shown in, for example, FIG. 6, in the present embodiment, the proximal end part 341 supports the driven-side bevel gear 117 so as to be integrally rotated around the pivot axis Y and, thereby, the driven-side bevel gear 117 and the proximal end part 341 are integrally rotated around the pivot axis Y by rotational power from the driver 110.

In the present embodiment, the proximal end part 341 is in a substantially upright flat plate form.

As shown in FIGS. 4 and 6, a distal end surface 346 of the distal end part 345 forms an opposing surface facing the outer surface of the first lower leg frame 40(1) facing outward in the user width direction.

The distal end surface 346 has a predetermined length in a width direction D corresponding to the width direction of the first lower leg frame 40(1) (i.e., the user front-back direction).

In the present embodiment, the distal end part 345 is in a substantially horizontal flat plate form, and the distal end surface 346 is substantially rectangular.

As shown in FIGS. 4 and 6, the lower connecting body 370 has a support hole 371 formed in the distal end part 345, an engagement pin 372 accommodated in the support hole 371 so as to capable of advancing and retreating, a biasing spring 373 for biasing the engagement pin 372, and an engagement arm 375 provided on the distal end part 345.

The support hole 371 is open to the opposing surface in an intermediate region in the width direction of the opposing surface and extends in a direction substantially perpendicular to the outer surface of the first lower leg frame 40(1).

The engagement pin 372 is accommodated in the support hole 371 so as to be axially movable such that the engagement pin 372 can take a projecting position where the distal end of the engagement pin 372 projects from the opposing surface and a retreated position where the engagement pin 372 is inserted deep into the support hole 371 so as to be away from the first lower leg frame 40(1) than it is at the projecting position.

The biasing spring 373 biases the engagement pin 371 toward the projecting position.

In the present embodiment, the biasing spring 373 is interposed between the proximal end part of the engagement pin 372 and the back surface of the support hole 371.

Specifically, in the present embodiment, the support hole 371 is formed in the distal end part 345 such that one end side is open to the opposing surface and the other end side is open to the back surface opposite the opposing surface, and the other end side of the support hole 371 is closed by a closing plate 348 fixed to the back surface of the distal end part 345. In this case, the closing plate 348 forms the back surface of the support hole 371.

The engagement arm 375 has an axially extended part 376 extending along the pivot axis Y from the opposing surface toward the first lower leg frame 40(1).

A width-direction separating distance between the axially extended part 376 and the engagement pin 372 is set such that the first lower leg frame 40(1) can be disposed between the axially extended part 376 and the engagement pin 372 with respect to the width direction of the lower frame 340.

That is, the width-direction separating distance between the engagement pin 372 and the axially extended part 376 is greater than the width of the first lower leg frame 40(1) such that the first lower leg frame 40(1) can be positioned between the engagement pin 372 and the axially extended part 376 with respect to the user front-back direction.

Here, an operation for attaching the lower frame 340 to the first lower leg frame 40(1) by the lower connecting body 370 will now be described.

Figure 7:
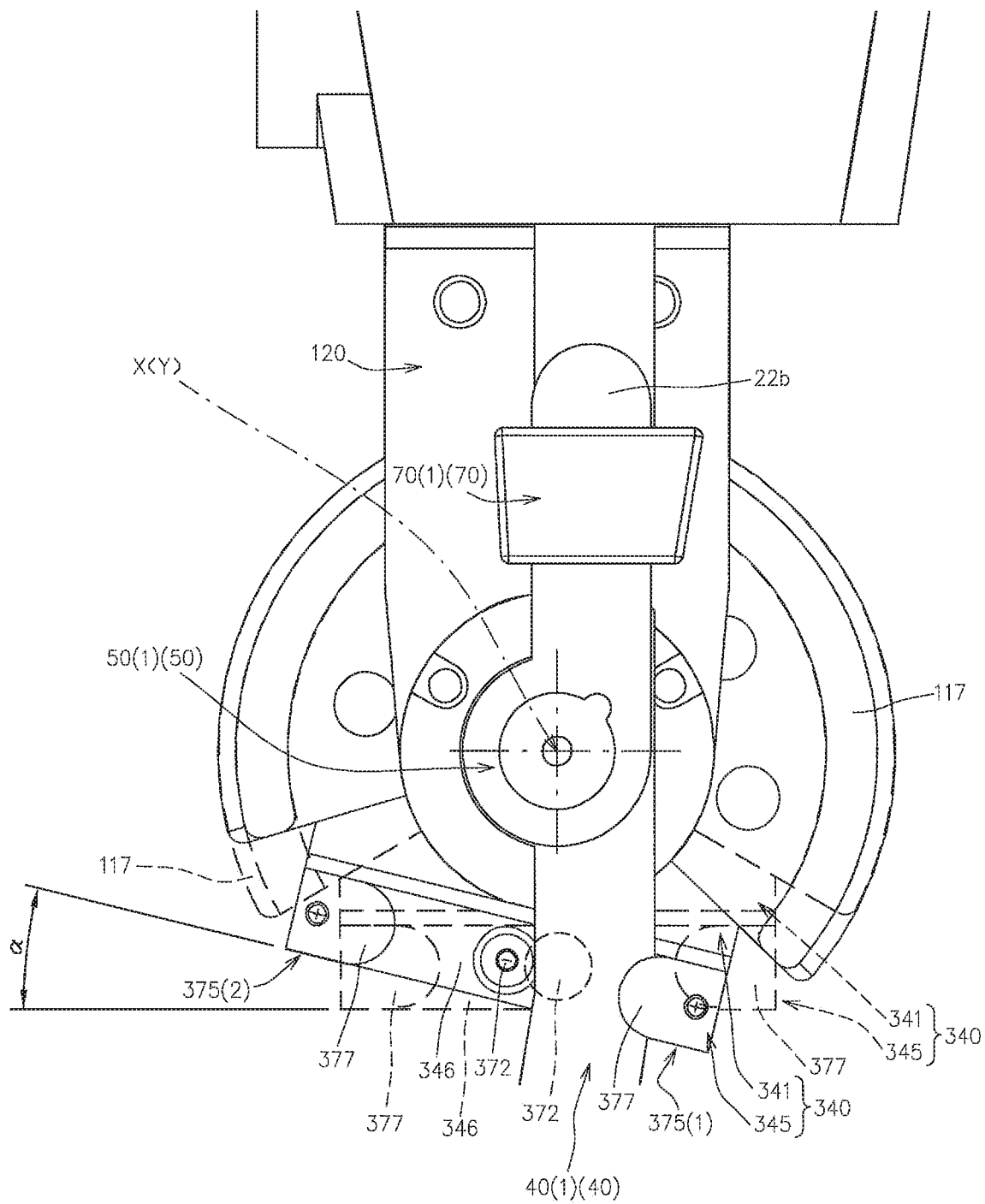
FIG. 7 is an end view taken along a line VII-VII in FIG. 2.

FIG. 7 shows an end view taken along a line VII-VII in FIG. 2.

When connecting the lower frame 340 to the first lower leg frame 40(1) by the lower connecting body 370, first the actuator unit 100 is moved in the pivot axis Y direction relative to the knee ankle foot orthosis body to a position where the first lower leg frame 40(1) overlaps the axially extended part 376 with respect to the direction parallel to the pivot axis Y, while positioning the engagement pin 372 in the retreated position against the biasing force of the biasing spring 373.

At this time, preferably, movement of the engagement pin 372 to the retreated position can be performed via the outer surface of the first lower leg frame 40(1).

That is, the actuator unit 100 can be relatively moved toward the first lower leg frame 40(1) such that the engagement pin 372 is moved from the projecting position to the retreated position, with the outer surface of the first lower leg frame 40(1) being in contact with the engagement pin 372.

This state is indicated by broken lines in FIG. 7.

From the state indicated by broken lines in FIG. 7, rotating the lower frame 340 in a connecting direction around the pivot axis Y (the clockwise direction in FIG. 7) cancels contact between the engagement pin 372 and the first lower leg frame 40(1), and brings the engaging pin 372 from the retreated position to the projecting position due to the biasing force of the biasing spring 373.

Accordingly, the first lower leg frame 40(1) is sandwiched between the engagement pin 372 and the axially extended part 376 with respect to the width direction of the lower frame 340 (the user front-back direction) (see solid lines in FIG. 7). Thus, an interlocking state is attained where the first lower leg frame 40(1) is rotated around the swing axis X relative to the thigh frame 20 in conjunction with the rotational movement of the lower frame 340 around the pivot axis Y relative to the upper frame 120 with the lower frame 340 being relatively movable in the longitudinal direction of the frame relative to the first lower leg frame 40(1).

By reversing the operation performed during attachment, the lower frame 340 connected to the first lower leg frame 40(1) by the lower connecting body 370 can be detached.

That is, when the lower frame 340 is connected to the first lower leg frame 40(1) by the lower connecting body 370, the engagement pin 372 is positioned in the projecting position due to the biasing force of the biasing spring 373.

By pressing the engagement pin 372 in the projecting position to the retreated position against the biasing force of the biasing spring 373 by manual operational force and rotating the lower frame 340 in the cancelling direction around the pivot axis Y (the counterclockwise direction in FIG. 7), a state where the distal end part of the engagement pin 372 is in contact with the outer surface of the first lower leg frame 40(1) is attained (the state indicated by broken lines in FIG. 7).

Thereafter, by relatively moving the first lower leg frame 40(1) and the lower frame 340 in mutually separating directions, the lower frame 340 can be detached from the first lower leg frame 40(1).

Preferably, the engagement arm 375 includes a width-direction extending part 377 extending from the axially extended part 376 toward the engagement pin 372 with respect to a width direction W of the opposing surface and facing the inner surface of the first lower leg frame 40(1) (the side surface facing inward relative to the user's width direction) in a state where the lower frame 340 is connected to the first lower leg frame 40(1).

The width direction extending part 377 is configured such that the axially separating distance between the width direction extending part 377 and the distal end surface 346 is greater than the thickness of the first lower leg frame 40(1) such that the first lower leg frame 40(1) can be disposed in a retaining space 370S (see FIG. 4) surrounded by the engagement pin 372, the distal end surface 346 forming the opposing surface, the axially extended part 376, and the width-direction extending part 377.

By providing the engagement arm 375 with the width-direction extending part 377, the lower frame 340 and the first lower leg frame 40(1) can be effectively prevented from relatively moving away from each other in the pivot axis Y directions when the lower frame 340 is connected to the first lower leg frame 40(1) by the lower connecting body 370.

Accordingly, unintentional detachment of the lower frame 340 from the first lower leg frame 40(1) can be effectively prevented.

In the present embodiment, the engaging arm 375 has first and second engagement arms 375(1), 375(2) respectively provided on one side and the other side in the width direction of the opposing surface, and is capable of connecting the lower frame 340 to the first lower leg frame 40(1) even when the lower frame 340 is rotated in any direction around the pivot axis Y from the state indicated by broken lines in FIG. 7.

Moreover, in the present embodiment, as shown in FIG. 7, the swing axis X is off-center toward one side in the width direction (the user front-back direction) of the first lower leg frame 40(1) relative to the center in the width direction (the user front-back direction) of the first lower leg frame 40(1). In FIG. 7, the swing axis X is off-center toward the back with respect to the user front-back direction relative to the width direction center of the first lower leg frame 40(1).

In this case, the actuator unit 100 can be attached to any of the left foot side and the right foot side of the knee ankle foot orthosis 1 by disposing the engagement pin 372 in the center in the width direction (the user front-back direction) of the lower frame 40 and configuring the engagement arm 375 to have the first and second engagement arms 375(1), 375(2) that are respectively positioned on one side and the other side in the width direction of the lower frame 40 (the front side and the back side with respect to the user front-back direction) with the engagement pin 372 in-between.

That is, when attaching the actuator unit 100 to the left foot side of the knee ankle foot orthosis 1, the first lower leg frame 40(1) can be sandwiched between the engagement pin 372 and the first engagement arm 375(1), and when attaching the actuator unit 100 to the right foot side of the knee ankle foot orthosis 1, the first lower leg frame 40(1) can be sandwiched between the engagement pin 372 and the second engagement arm 375(2).

In the present embodiment, as shown in FIG. 7, the actuator unit 100 is attached such that the first lower leg frame 40(1) is sandwiched between the engagement pin 372 and the first engagement arm 375(1) positioned on the front side with respect to the user front-back direction, but when it is desired to increase the rotational angle of the first lower leg frame 40(1) relative to the first thigh frame 20(1), the actuator unit 100 can be attached such that the first lower leg frame 40(1) is sandwiched between the engagement pin 372 and the second engagement arm 375(2) positioned on the back side with respect to the user front-back direction.

That is, when the first lower leg frame 40(1) is sandwiched between the engagement pin 372 and the first engagement arm 375(1) positioned on the front side with respect to the user front-back direction, the initial orientation of the lower frame 340 (the orientation of the lower frame 340 when a user is in substantially upright posture with the actuator unit 100 being attached, the orientation indicated by solid lines in FIG. 7) is an orientation reached by rotating the lower frame 340 a predetermined angle α in the clockwise direction around the pivot axis Y from the horizontal orientation (the orientation indicated by broken lines in FIG. 7) as viewed from inside in the user width direction.

Here, given the movement of the left leg when the user wearing the knee ankle foot orthosis 1 equipped with the actuator unit 100 on the left leg walks, the first lower leg frame 40(1) is rotated in the clockwise direction relative to the first thigh frame 20(1) as viewed from inside in the user width direction when performing the bending movement of the lower leg relative to the thigh.

Accordingly, in the initial orientation with the actuator unit 100 being attached to the knee ankle foot orthosis 1, assuming that the lower frame 340 is rotated the predetermined angle α in the clockwise direction around the pivot axis Y from a horizontal orientation (the orientation indicated by broken lines in FIG. 7) as viewed from inside in the user width direction, the range in which the lower leg can be pressed in the bending direction relative to the thigh to assist the user to perform knee bending movement, i.e., the rotation range in which the lower frame 340 can be rotated in the clockwise direction around the pivot axis Y as viewed from inside in the user width direction, is reduced to an extent corresponding to the predetermined angle α in reference to the horizontal orientation.

On the other hand, attaching the actuator unit 100 such that the first lower leg frame 40(1) is sandwiched between the engagement pin 372 and the second engagement arm 375(2) positioned on the back side with respect to the user front-back direction brings the lower frame 340 into an orientation wherein the lower frame 340 is rotated the predetermined angle α in the counterclockwise direction around the pivot axis Y from the horizontal orientation (the orientation indicated by broken lines in FIG. 7) as viewed from inside in the user thickness direction.

Accordingly, the range in which pressing force can be imparted in the knee bending direction to assist the user's gait movement, i.e., the rotation range in which the lower frame 340 can be rotated in the clockwise direction around the pivot axis Y as viewed from inside in the user width direction, can be increased to an extent corresponding to the predetermined angle α in reference to the horizontal orientation.

Here, the control structure for the knee ankle foot orthosis 1 according to the present embodiment will now be described.

The knee ankle foot orthosis 1 according to the present embodiment is configured to perform operational control for the actuator unit 100 that imparts gait assisting force to the lower leg, based on the thigh orientation of the user.

That is, the knee ankle foot orthosis 1 is configured to detect movement of the thigh, which is different from the lower leg which is a control target site, and perform operational control for the actuator unit 100 that imparts gait assisting force to the lower leg, which is a control target site, based on the movement of the thigh.

Specifically, as shown in FIGS. 1 and 3, the knee ankle foot orthosis 1 includes a thigh orientation detecting means 510 capable of detecting an angle-related signal concerning the thigh swing angle of the user, and a control device 500 managing operational control for the actuator unit 100.

The thigh orientation detecting means 510 is configured to detect the angle-related signal in a plurality of sampling points each at a predetermined timing during one gait cycle and send the angle-related signal to the control device 500.

The control device 500 includes a processing unit including a control processing means for executing processing based on a signal received from the thigh orientation detecting means 510, a manually operated member, or the like; and a storage unit including a ROM storing a control program, control data, and the like, a non-volatile storage means storing a setting value or the like such that the setting value or the like is not lost even when a power supply is interrupted and is rewritable, a RAM temporarily storing data generated during processing by the processing unit, or the like.

The control device 500 is configured to calculate a thigh phase angle at one sampling point based on the angle-related signal at that sampling point, apply the thigh phase angle at that sampling point to assisting force control data that is stored in the control device 500 in advance and that indicates the relationship between the thigh phase angle and the size of assisting force to be imparted to the lower leg-side brace to calculate the size of assisting force to be imparted to the lower leg-side brace 30 at that sampling point, and execute operational control for the actuator unit 100 such that assisting force having the calculated size is output.

That is, the control device 500 is configured to act as a thigh phase angle calculating means for calculating a thigh phase angle at one sampling point based on the angle-related signal at that sampling point, an assisting force calculating means for applying the thigh phase angle calculated by the thigh phase angle calculating means to assisting force control data indicating the relationship between the thigh phase angle and the size of assisting force to be imparted to the lower leg-side brace to calculate the size of assisting force to be imparted to the lower leg-side brace 30 at that sampling point, and an actuator operational control means for executing operational control for the actuator unit 100 such that assisting force having the size calculated by the assisting force calculating means is output.

Thus, by executing operation control for the actuator unit 100 to impart gait assisting force to the lower leg based on the phase angle of the thigh, suitable gait assisting force can be supplied even to a user with hemiplegia due to a stroke or the like.

That is, conventional gait assisting devices configured to impart gait assisting force by an actuator unit are configured to detect movement of a control target site to which assisting force is to be imparted by the actuator unit, and perform operational control for the actuator unit based on the detection result.

For example, in conventional gait assisting devices that supply gait assisting force to the thigh, operational control for the actuator that imparts gait assisting force to the thigh is performed based on the result of detecting thigh movement.

Moreover, in conventional gait assisting devices that supply gait assisting force to the lower leg, operational control for the actuator for imparting gait assisting force to the lower leg is performed based on the result of detecting lower leg movement.

However, in the case of a patient with hemiplegia due to a stroke or the like, gait motion of the lower leg (forward and backward swing motion around the knee joint) often cannot be performed normally, while gait motion of the thigh (forward and backward swing motion around the hip joint) can be performed relatively normally.

When attempting to impart gait assisting force to the lower leg of such a patient, in the above conventional gait assisting devices, operational control for the actuator that provides gait assisting force to the lower leg is performed based on the movement of the lower leg that is incapable of normal gait motion and, possibly, suitable gait assisting force cannot be provided.

On the other hand, the knee ankle foot orthosis 1 according to the present embodiment is configured to perform operational control for the actuator unit 100 to impart gait assisting force to the lower leg based on the thigh phase angle as described above.

Accordingly, even in the case of a user with hemiplegia due to a stroke or the like, suitable gait assisting force can be imparted to the lower leg.

The thigh orientation detecting means 510 may have various forms such as a gyro sensor, an acceleration sensor, and a rotary encoder as long as it can directly or indirectly detect the swing angle of the thigh (the hip joint angle).

For example, the thigh orientation detecting means 510 can be configured to have only an acceleration sensor, and in this case, the phase angle during walking can be calculated from the acceleration (or position) and speed of the acceleration sensor without calculating the hip joint angle.

In the knee ankle foot orthosis 1 according to the present embodiment, the thigh orientation detecting means 510 has a triaxial angular velocity sensor (a gyro sensor) 511 capable of detecting the angular velocity of the thigh (see FIG. 8), and the control device 500 calculates the hip joint angle by integrating the angular velocity of the thigh detected by the triaxial angular velocity sensor 511.

Thus, calculating the hip joint angle based on the angular velocity detected by the triaxial angular velocity sensor 511 enables enhanced design freedom of the knee ankle foot orthosis 1 to be provided as compared to a configuration in which the hip joint angle is detected by a rotary encoder.

That is, when detecting the hip joint angle by a rotary encoder, it is necessary to detect the angle of relative movement between a torso-side detector fixed to the torso and a thigh-side detector fixed to the thigh so as to swing integrally with the thigh, and it is therefore necessary to attach both detectors such that the torso-side detector and the thigh-side detector do not positionally shift relative to the torso and the thigh, respectively.

On the other hand, the method of calculating the hip joint angle based on an angular velocity detected by the triaxial angular velocity sensor 511 does not have the above-described restrictions and can provide enhanced design freedom of the knee ankle foot orthosis 1.

Figure 8:
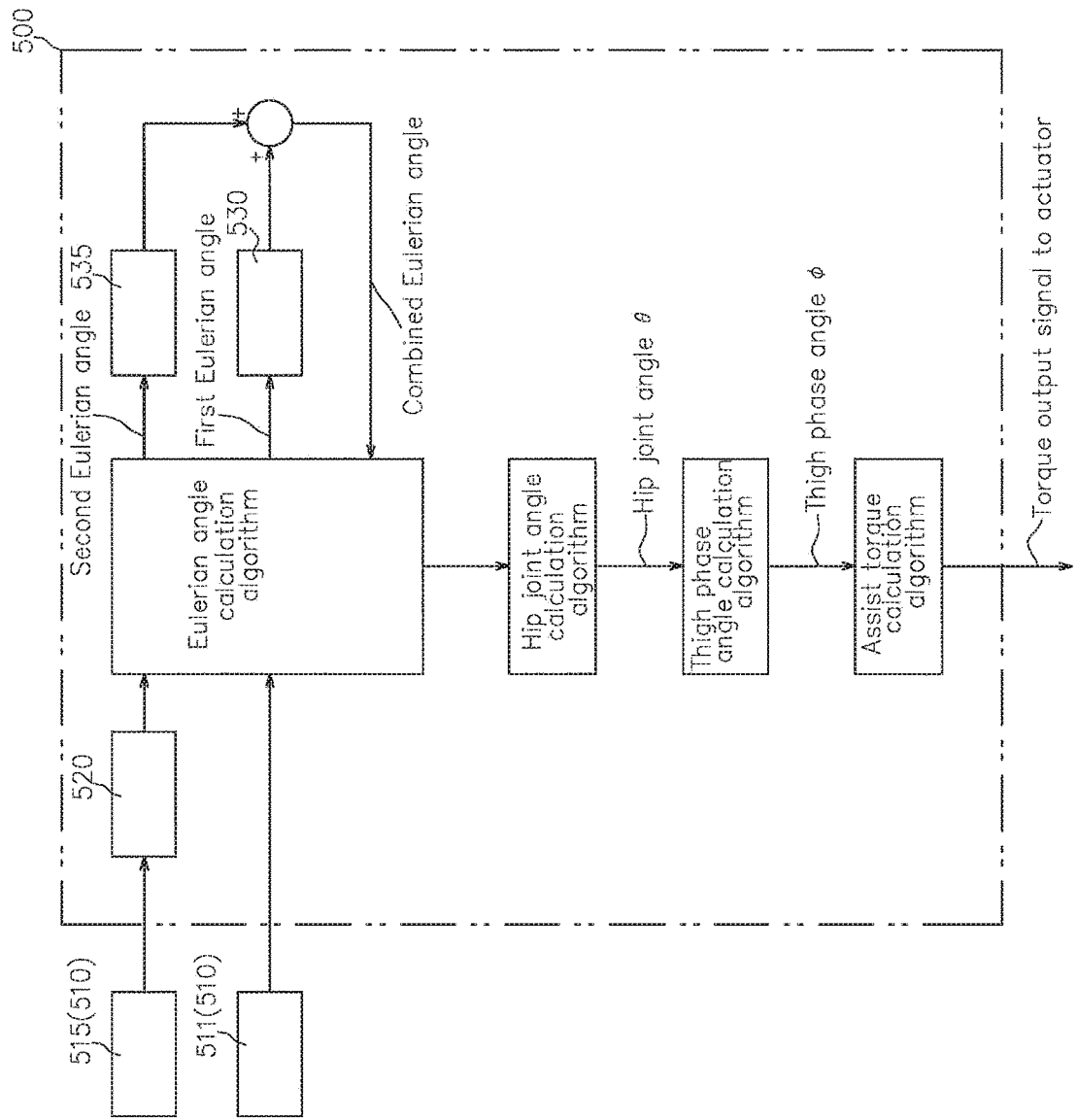
FIG. 8 is a block diagram regarding a method of calculating a hip joint angle of the knee ankle foot orthosis.

FIG. 8 shows a block diagram of the method of calculating a hip joint angle.

As shown in FIG. 8, in the knee ankle foot orthosis 1 according to the present embodiment, the thigh orientation detecting means 510 has a triaxial acceleration sensor 515 in addition to the triaxial angular velocity sensor 511.

In this case, the control device 500 is configured to calculate a combined Eulerian angle by combining a high-frequency component of a first Eulerian angle calculated based on angular velocity data from the triaxial angular velocity sensor 511 and a low-frequency component of a second Eulerian angle calculated based on acceleration data from the triaxial acceleration sensor 515, and calculate a thigh phase angle based on a hip joint angle calculated from the combined Eulerian angle and a hip joint angular velocity calculated from the hip joint angle.

Specifically, as shown in FIG. 8, the control device 500 receives sensor coordinate axis-based angular velocity data from the triaxial angular velocity sensor 511 at every predetermined sampling time, and converts the angular velocity data into angular velocity data (Eulerian angular velocity) that indicates a correlation between a sensor coordinate axis and a global coordinate axis (a spatial coordinate axis based on the vertical direction) using a predetermined conversion formula.

Then, the control device 500 integrates the angular velocity data (Eulerian angular velocity) to calculate the first Eulerian angle.

Preferably, the control device 500 can perform drift elimination on sensor coordinate axis-based angular velocity data received from the triaxial angular velocity sensor 511 at every predetermined sampling time using angular velocity data received from the triaxial angular velocity sensor 511 when the user is at rest.

Moreover, the control device 500 receives sensor axis-based acceleration data from the triaxial acceleration sensor 515 at every predetermined sampling interval via a low-pass filter 520, and calculates the second Eulerian angle indicating a correlation between a sensor coordinate axis and a global coordinate axis (a vertical direction-based spatial coordinate axis) from the acceleration data received via the low-pass filter 520, based on acceleration data received when at rest and gravitational acceleration.

Then, the control device 500 calculates a hip joint angle θ from a unit vector indicating the orientation of the thigh and the combined Eulerian angle obtained by combining the high-frequency component of the first Eulerian angle obtained via a high-pass filter 530 and the low-frequency component of the second Eulerian angle obtained via the low-pass filter 535.

Preferably, the control device 500 can perform drift elimination by detecting heel contact based on acceleration data from the acceleration sensor 515 and, when heel contact is detected, adding a corrected Eulerian angle calculated from angular velocity data from the triaxial angular velocity sensor 511 to the combined Eulerian angle.

A thigh phase angle (p is calculated by the following method.

The control device 500 calculates a hip joint angle θn at the $n^{th}$ sampling point Sn (n is an integer of 1 or greater) from a gait cycle reference timing among sampling points at predetermined intervals, and then differentiates it to calculate a hip joint angular velocity ωn at the sampling point Sn.

Thereafter, the control device 500 calculates a thigh phase angle φn (=−Arctan(ωn/θn)) at the sampling point Sn based on the hip joint angle θn and the hip joint angular velocity ωn at the sampling point Sn.

Figure 9:
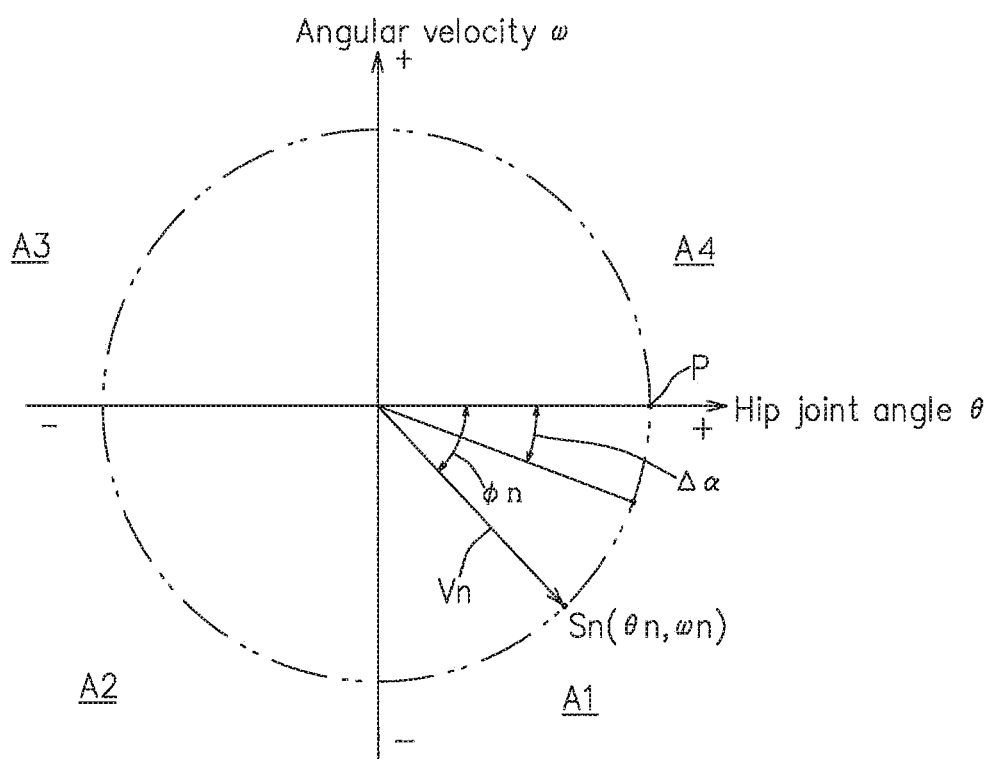
FIG. 9 is a trajectory diagram obtained by plotting hip joint angle θ and the hip joint angular velocity ω, which are calculated by a control device of the knee ankle foot orthosis, over one gait cycle.

FIG. 9 shows a trajectory diagram obtained by plotting gait states defined by the hip joint angle θ and the hip joint angular velocity ω over one gait cycle.

As shown in FIG. 9, the thigh phase angle φ determined by the hip joint angle θ and the hip joint angular velocity ω is defined so as to vary between 0 and 2π in one gait cycle.

Specifically, the hip joint angle in a state where the thigh is positioned in front of and behind the user's body axis is referred to as "positive" and "negative", respectively, and the hip joint angular velocity in a state where the thigh is swung forward and backward is referred to as "positive" and "negative", respectively.

Under this condition, if the phase angle in a state where the hip joint angle is largest in the "positive" direction and the hip joint angular velocity is "zero" (point P in FIG. 9) is regarded as 0, a gait area A1 in FIG. 9 (a gait area from a state where the hip joint angle θ is largest in the "positive" direction and the hip joint angular velocity ω is "zero" to a state where the hip joint angle θ is "zero" and the hip joint angular velocity ω is largest in the "negative" direction) corresponds to the phase angle of 0 to π/2.

Moreover, a gait area A2 in FIG. 9 (a gait area from a state where the hip joint angle θ is "zero" and the hip joint angular velocity is largest in the "negative" direction to a state where the hip joint angle is largest in the "negative" direction and the hip joint angular velocity is "zero") corresponds to the phase angle of π/2 to π.

Furthermore, a gait area A3 in FIG. 9 (a gait area from a state where the hip joint angle θ is largest in the "negative" direction and the hip joint angular velocity ω is "zero" to a state where the hip joint angle θ is "zero" and the hip joint angular velocity ω is largest in the "positive" direction) corresponds to the phase angle of π to 3π/2.

Also, a gait area A4 in FIG. 9 (a gait area from a state where the hip joint angle θ is "zero" and the hip joint angular velocity is largest in the "positive" direction to a state where the hip joint angle is largest in the "positive" direction and the hip joint angular velocity is "zero") corresponds to the phase angle of $3\pi/2$ to $2\pi$.

The sampling interval of the thigh orientation detecting means 510 is determined such that a plurality of sampling points are included in one gait cycle, and the control device 500 calculates the thigh phase angle φ at each sampling point.

Figure 10:
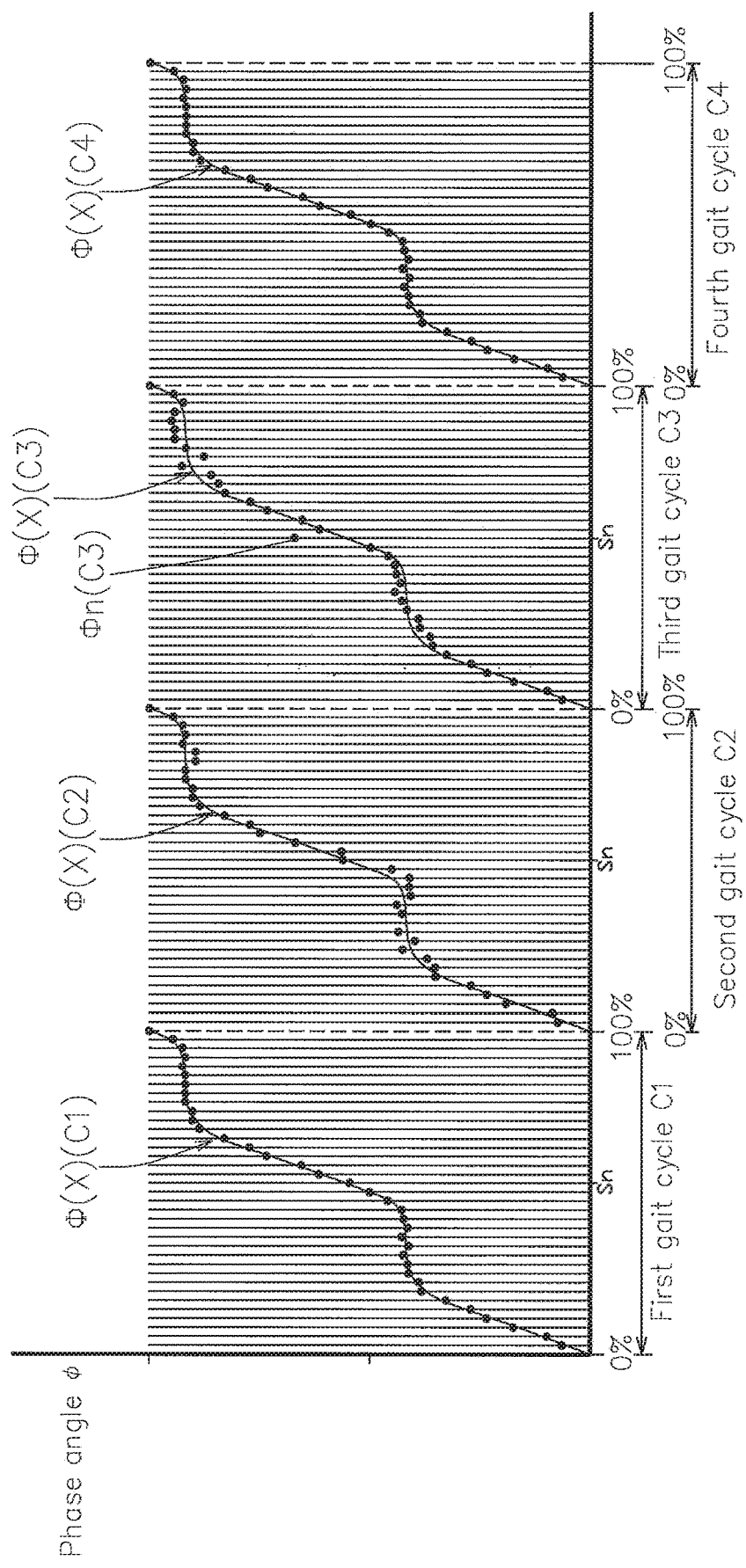
FIG. 10 is a graph obtained by plotting thigh phase angles φ calculated by the control device for each gait cycle.

FIG. 10 shows a graph obtained by plotting the thigh phase angles φ calculated by the control device 500 for each gait cycle.

In FIG. 10, the thigh phase angles (p in four gait cycles from a first gait cycle C1 to a fourth gait cycle C4 are plotted.

Here, assisting force control data is stored in the control device 500 in advance that indicates the relationship between the thigh phase angle φ and the size (including the direction) of gait assisting force by the actuator unit 100 to be output to the lower leg.

The assisting force control data is set for each user and for each level of rehabilitation of the user by experimentation or the like.

That is, the control device 500, having calculated a thigh phase angle φn at one sampling point Sn, applies the thigh phase angle φn to the assisting force control data to obtain the size (including the direction) of gait assisting force to be output by the actuator unit 100 during a gait state defined by the thigh phase angle φn, and executes operational control for the actuator unit 100 such that gait assisting force having that size (including the direction) is output.

As described above, gait states during one gait cycle can be recognized based on the thigh phase angle φ and, accordingly, by performing operational control for the actuator unit 100 based on the thigh phase angle, appropriate gait assisting force can be imparted to the lower leg even for a user having difficulty in performing normal gait motion of the lower leg.

Here, gait assisting force required for gait motion will now be described.

Figure 11:
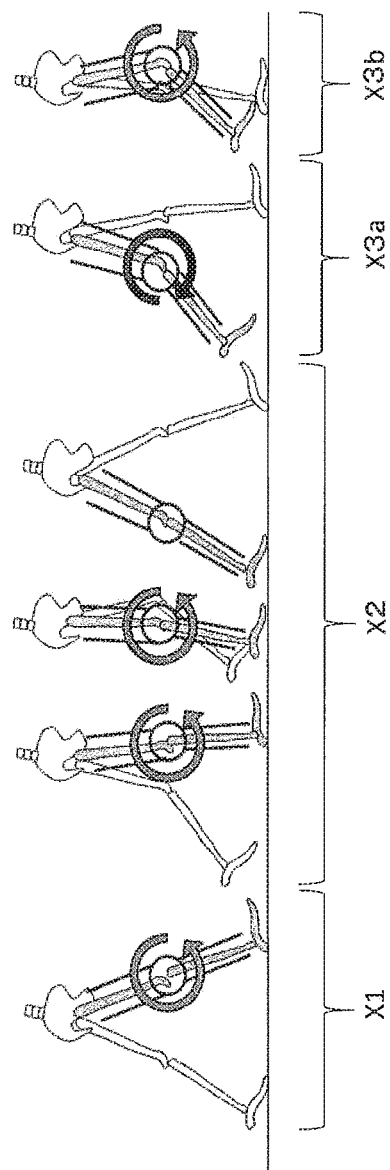
FIG. 11 is a schematic diagram of gait states that change during one gait cycle.

FIG. 11 shows a schematic diagram of gait states that change during one gait cycle.

As shown in FIG. 11, one gait cycle includes a heel contact phase X1 including a heel contact time point when the heel contacts the ground in front of the user's body axis (a period before and after the forward-raised foot contacts the floor), a stance phase X2 when the heel-contacted leg after heel contact is relatively moved backward while being in contact with the ground (a period when the floor-contacted lower limb is relatively moved backward relative to the body), and a swing phase X3 when the leg contacting the ground since the end of stance phase X2 is raised and relatively moved forward.

Figure 12:
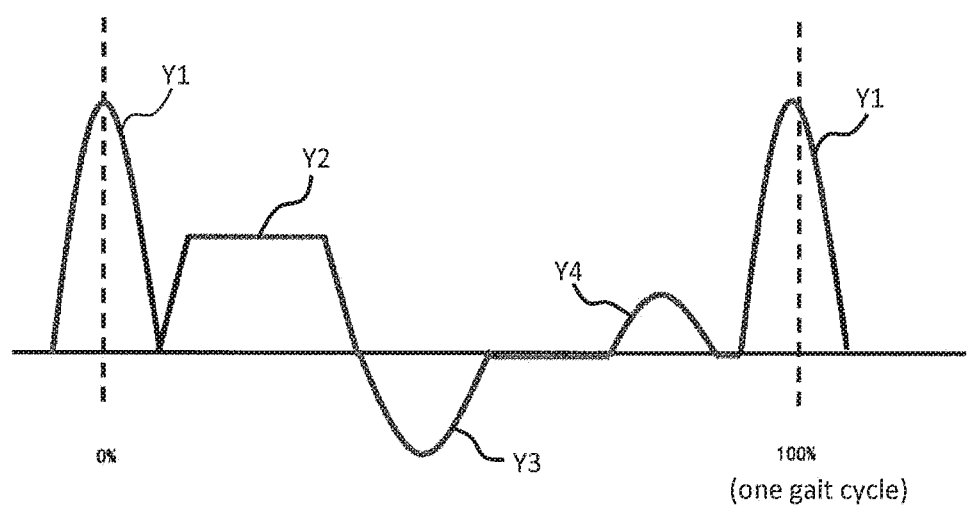
FIG. 12 is a graph showing one example of an assisting force control data indicating a relationship between gait states during one gait cycle and an assisting force to be output by the actuator unit.

FIG. 12 shows one example of the change pattern of assisting force defined by the assisting force control data.

In the example shown in FIG. 12, the assisting force control data includes a first torque pattern Y1 for preventing knee bending by rotating the lower leg-side brace 30 in the knee extending direction around the knee joint in the heel contact phase X1, a second torque pattern Y2 for preventing knee bending by rotating the lower leg-side brace 30 in the knee extending direction around the knee joint in the stance phase X2, a third torque pattern Y3 for assisting the raising of the leg by rotating the lower leg-side brace 30 around the knee joint in the knee bending direction in an initial stage X3a of the swing phase X3 wherein the leg contacting the ground since the end of the stance phase X2 is raised and relatively moved forward, and a fourth torque pattern Y4 for rotating the lower leg-side brace 30 around the knee joint in the knee extending direction in a later stage X3b of the swing phase X3.

Thus, by performing operational control for the actuator unit 100 using the assisting force control data indicating the relationship between the thigh phase angle φ and the gait assisting force, gait assistance appropriate for a user can be performed.

Preferably, the control device 500 may be configured to calculate a corrected phase angle φ(ave) obtained by correcting the thigh phase angle φn calculated at one sampling point Sn in the current gait cycle using the thigh phase angle at the corresponding sampling point Sn in previous gait cycles that have already been completed, and apply the corrected phase angle φ(ave) to the assisting force control data to perform operational control for the actuator unit 100.

According to this configuration, even when the thigh phase angle φn (current) calculated at one sampling point Sn in the current gait cycle includes a great error for some reason, the thigh phase angle φn(current) is corrected (averaged) using the thigh phase angle φn(past) at the same sampling point Sn in previous gait cycles, and thus assisting force can be smoothly supplied.

Specifically, the corrected phase angle φ(ave) can be calculated by the following method.

The control device 500 calculates and stores the thigh phase angles φ at all sampling points included in one gait cycle.

Then, upon detecting completion of one gait cycle, the control device 500 calculates using the least-squares method a predetermined phase pattern function indicating the change pattern of the thigh phase angles φ concerning the gait cycle based on the thigh phase angles φ at all sampling points.

The phase pattern function can be, for example:

$$\varphi(x)=a+bx+cx^2+dx^3+ex^4+fx^5$$

The control device 500 is configured to calculate coefficients a to f of the phase pattern function using the least-squares method based on the thigh phase angles at all sampling points every time one gait cycle is completed.

Completion of one gait cycle can be determined by the control device 500, for example, based on whether or not the gait state defined by the hip joint angle and the hip joint angular velocity has returned to a predetermined gait cycle reference timing.

Thus, by setting heel contact as a gait cycle reference timing, a timing at which gait assisting force is needed during a gait cycle can be precisely recognized.

The timing of heel contact can be recognized by various methods.

For example, if the hip joint angular velocity when the thigh swings forward and backward in reference to the user's body axis is referred to as positive and negative, respectively, the control device 500 can be configured to recognize as the heel contact timing the time point at which the calculated hip joint angular velocity advances a predetermined phase angle Act from the timing (P in FIG. 9) at which the calculated hip joint angular velocity reaches zero from a positive value.

Alternatively, it is possible to provide the knee ankle foot orthosis 1 with a heel contact detecting means for detecting heel contact, and configure the control device 500 to recognize a timing detected by the heel contact detecting means as a heel contact time point and recognizes the thigh phase angle φ at that timing as a heel contact phase angle.

When the acceleration sensor 515 is provided as in the knee ankle foot orthosis 1 according to the present embodiment, the acceleration sensor 515 can be used as the heel contact detecting means as well.

Alternatively, it is also possible to separately provide a pressure sensor capable of detecting ground contact of the heel and cause the pressure sensor to act as the heel contact detecting means.

When the control device 500 detects completion of one gait cycle in this manner, the control device 500 calculates the phase pattern function based on the phase angles in already completed gait cycles including the most recently completed gait cycle.

Specifically, when the gait cycle C1 in FIG. 10 is completed, the control device 500 calculates:

$$\varphi(x)(C1)=a(1)+b(1)x+c(1)x^2+d(1)x^3+e(1)x^4+f(1)x^5$$

based on the thigh phase angles φ at all sampling points in the gait cycle C1, and saves φ(x)(C1) as a phase pattern function of the thigh phase angle.

When the gait cycle C2 is completed, the control device 500 calculates:

$$\varphi(x)(C2)=a(2)+b(2)x+c(2)x^2+d(2)x^3+e(2)x^4+f(2)x^5$$

based on the thigh phase angles at sampling points in the gait cycle C2 and the thigh phase angles at the sampling points in the gait cycle C1, and overwrites φ(x)(C2) as a phase pattern function of the thigh phase angle.

Specifically, in the second and subsequent gait cycles, the control device 500 calculates, as a corrected thigh phase angle φn(ave) at the sampling point Sn, the average value of the thigh phase angle φn(current) at the sampling point Sn in the current gait cycle (e.g., the gait cycle C2) and the thigh phase angle φn(past) at the sampling point Sn in previous gait cycles calculated with the phase pattern function φ(x)(C1) stored at that time.

When the current gait cycle (e.g., the gait cycle C2) is completed, the control device 500 calculates the phase pattern function (e.g., φ(x)(C2)) based on the corrected thigh phase angles at all sampling points and saves it.

As the average value of the thigh phase angle φn(current) at the sampling point Sn in the current gait cycle and the thigh phase angle φn(past) at the corresponding sampling point Sn in previous gait cycles, it is also possible to use a calculated value obtained by averaging equally-weighted thigh phase angles in all gait cycles including the current gait cycle and the previous gait cycles, alternatively it is also possible to use a calculated value obtained by weighting the thigh phase angle φn(current) of the current gait cycle and taking an average, and alternatively it is also possible to use a calculated value obtained by weighting the thigh phase angle φn(past) in the previous gait cycles and taking an average.

Furthermore, it is also possible to correct the thigh phase angle of the current gait cycle using only the thigh phase angles at sampling points in a predetermined gait cycle among the previous gait cycles.

In the present embodiment, the corrected thigh phase angle is used as a thigh phase angle to be applied to the assisting force control data.

For example, assuming that the current gait cycle is gait cycle C3 and that the thigh phase angle at the sampling point Sn in the current gait cycle C3 is φn(C3), the control device 500 calculates the thigh phase angle φn(C2) at the sampling point Sn in previous gait cycles using the phase pattern function stored at that time point (φ(x)(C2) in this example), and calculates the corrected thigh phase angle at the sampling point Sn based on the thigh phase angle φn(C3) and the thigh phase angle φn(C2).

The control device 500 applies the corrected thigh phase angle thus calculated to the assisting force control data to obtain the size (and the direction) of assisting force to be output by the actuator unit 100 at the sampling point Sn in the current gait cycle C3, and performs operational control for the actuator unit 100.

According to this configuration, even when the thigh phase angle calculated at one sampling point in the current gait cycle (gait cycle C3 in the above example) includes a great error for some reason, the thigh phase angle is corrected (averaged) using the thigh phase angle at the same sampling point Sn in previous gait cycles, and suitable assisting force can be supplied by the actuator unit 100.

Figure 13:
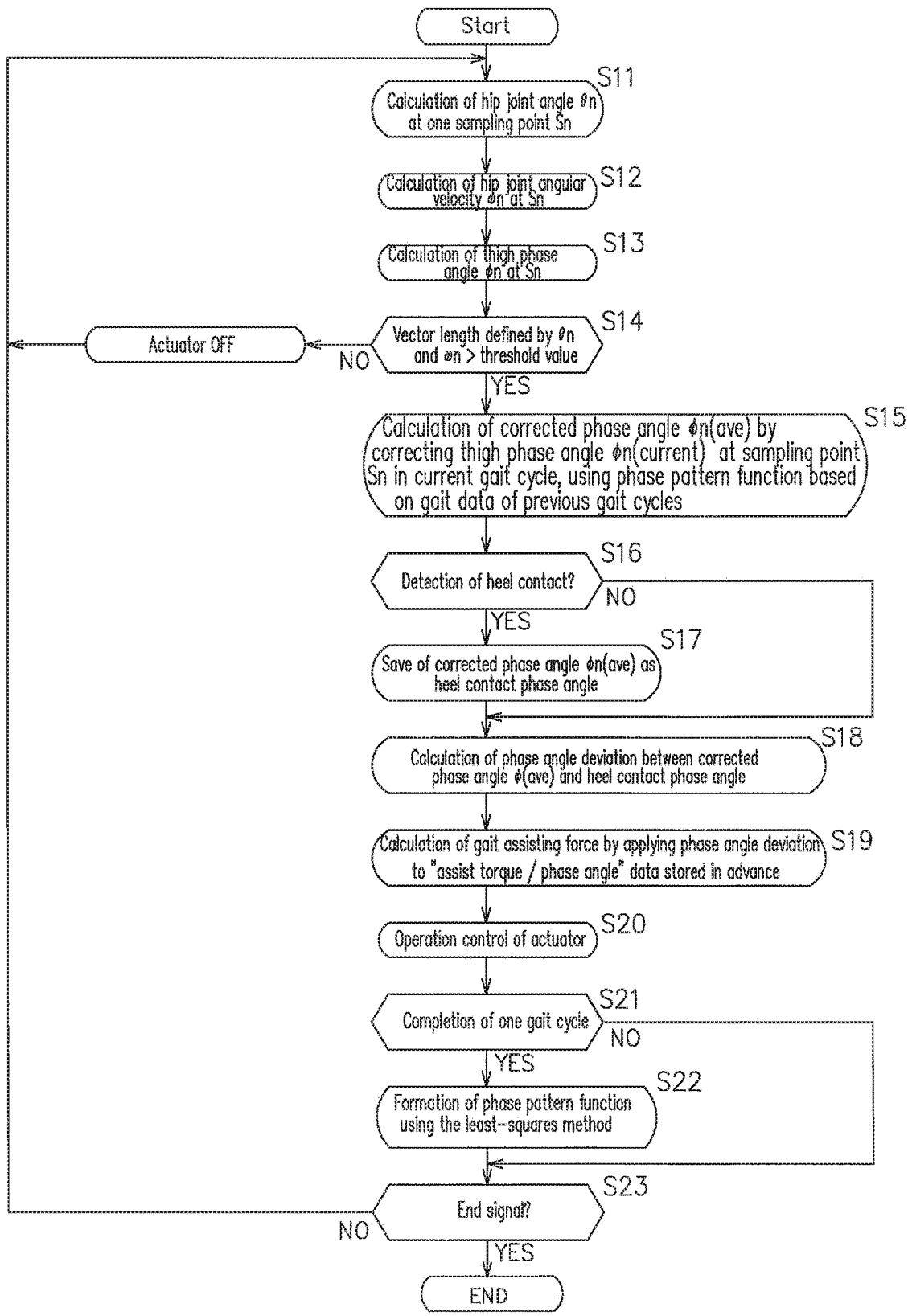
FIG. 13 is a flowchart of an actuator operational control mode executed by the control device.

FIG. 13 shows the flow of an actuator operational control mode executed by the control device 500.

The control device 500 activates the actuator operational control mode in response to an activation signal input.

The activation signal is input in response to, for example, manual operation by a user on a manually operated member such as a start button.

When the actuator operational control mode is activated, the control device 500 calculates a hip joint angle θn at one sampling point Sn based on an angle-related signal at that sampling point Sn from the thigh orientation detecting means 510 (step S11), and calculates a hip joint angular velocity ωn at that sampling point Sn based on the hip joint angle θn (step S12).

The control device 500 calculates a thigh phase angle φn at that sampling point Sn based on the hip joint angle θn and the hip joint angular velocity ωn (step S13).

Here, preferably, the control device 500 can determine whether or not the vector length of a vector Vn (see FIG. 9) defined by the hip joint angle θn and the hip joint angular velocity ωn exceeds a predetermined threshold value (step S14).

Due to step S14, it is possible to effectively prevent the actuator unit 100 from being operated even when gait motion is not started.

That is, a user with hemiplegia or the like is likely to unintentionally change posture over a small range before starting gait motion.

Such a minor posture change is detected as a vector having a short vector length.

Accordingly, by determining that gait motion is being performed only when the vector length of the vector Vn (see FIG. 9) defined by the hip joint angle θn and the hip joint angular velocity ωn exceeds a predetermined threshold value, it is possible to effectively prevent the actuator unit 100 from being unintentionally operated when gait motion is not started.

If NO in step S14, the control device 500 determines that gait motion is not being performed, and returns to step S11 without activating the actuator unit 100.

If YES in step S14, the control device 500 corrects the thigh phase angle φn(current) at the sampling point Sn in the current gait cycle calculated in step S13, by using the thigh phase angle φn(past) at the corresponding sampling point Sn in already completed previous gait cycles, to calculate the corrected phase angle φn(ave) (Step S15).

For example, in the case of having already calculated and overwrite-saved the phase pattern function every time the gait cycle ended based on gait data of previous gait cycles, the control device 500 can calculate the corrected phase angle φn(ave) at the sampling point Sn based on the thigh phase angle φn(current) at the sampling point Sn in the current gait cycle and the thigh phase angle at the sampling point Sn in previous gait cycles obtained based on the phase pattern function.

Due to step S15, even when the thigh phase angle calculated at one sampling point in the current gait cycle includes a great error for some reason, the thigh phase angle is corrected (averaged) using the thigh phase angle at the same sampling point Sn in previous gait cycles, and thus gait assisting force appropriate for that gait stage can be supplied.

The control device 500 detects whether or not heel contact has been made (step S16) and, if YES in step S16 (i.e., if heel contact has been made), stores the corrected phase angle calculated in step S15 as a heel contact phase angle corresponding to the heel contact (step S17), and advances to step S18.

In step S18, the control device 500 calculates a phase angle deviation between the corrected phase angle φ(ave) calculated in step S15 and the heel contact phase angle stored in step S17.

That is, in step 18, the control device 500 converts the corrected phase angle calculated in step S15 into a phase angle for which heel contact is used as a control reference timing.

Thus, by using heel contact as a control reference timing, a gait stage (a gait state) in a gait cycle can be recognized more appropriately.

When the processing advances to step 18 via step 17, the phase angle deviation is zero.

On the other hand, when the processing advances to step 18 by bypassing step 17, i.e., if NO in step 16, the deviation between the corrected phase angle calculated in step 15 and the heel contact phase angle stored at that time point becomes the phase angle deviation in step S18.

The control device 500 applies the phase angle deviation to "assist torque/phase angle" data stored in advance to obtain the size and direction of gait assisting force to be output by the actuator unit 100 at the sampling point Sn (step S19), and causes the actuator unit to be operated such that gait assisting force having that size and direction is output (step S20).

The control device 500 determines whether or not one gait cycle is finished (step S21) and, when determines that one gait cycle is finished, calculates a phase pattern function using the least-squares method on the modified phase angle and stores it (step S22).

If one gait cycle is not yet finished, step S22 is bypassed.

The control device 500 determines whether or not an end signal for the actuator operational control mode is input (step S23) and, if no end signal is input, returns to step S11, and if an end signal is input, terminates the control mode.

The end signal is input in response to, for example, a manual operation by a user on a manually operated member such as an end button.

DESCRIPTION OF THE REFERENCE NUMERALS

1 Knee ankle foot orthosis
10 Thigh-side brace
30 Lower leg-side brace
100 Actuator unit
500 Control device
510 Thigh orientation detecting means
511 Triaxial angular velocity sensor
515 Triaxial acceleration sensor

The invention claimed is:

1. An actuator-equipped knee ankle foot orthosis comprising: a thigh-side brace to be attached to a user's thigh; a lower leg-side brace to be attached to the user's lower leg, the lower leg-side brace being connected to the thigh-side brace so as to be rotatable around the user's knee joint; an actuator unit attached to the thigh-side brace and capable of imparting assisting force around the user's knee joint to the lower leg-side brace; a thigh orientation detecting means capable of detecting an angle-related signal concerning a hip joint angle that is a forward and backward swing angle of the user's thigh, wherein the thigh orientation detecting means comprises a triaxial angular velocity sensor configured to detect an angular velocity of the user's thigh and a triaxial acceleration sensor configured to detect an acceleration of the user's thigh; and a control device configured to manage operational control for the actuator unit, wherein for each gait cycle, the control device calculates a first Euler angle based on angular velocity data that is obtained by performing drift elimination on the angular velocity data received from the triaxial angular velocity sensor using angular velocity data from the triaxial angular velocity sensor when the user is at rest, calculates a second Euler angle calculated based on acceleration data from the triaxial acceleration sensor, and then calculates a combined Euler angle by combining a high-frequency component of the first Euler angle and a low-frequency component of the second Euler angle, wherein the control device calculates a thigh phase angle based on a hip joint angle calculated from the combined Euler angle and a hip joint angular velocity calculated from the hip joint angle, wherein the hip joint angle is not measured directly from a hip joint, wherein the control device obtains an assisting force to be imparted to the lower leg-side brace by applying the thigh phase angle to an assisting force control data, which is stored in the control device in advance and indicates a relationship between the thigh phase angle and a size of the assisting force to be imparted to the lower leg-side brace, wherein the control device controls the actuator unit to output the assisting force, and wherein the control device inhibits an operation of the actuator unit in a case where a length of a vector defined by the hip joint angle and the hip joint angular velocity that has been used when calculating the thigh phase angle is between zero and the predetermined threshold value.

2. The actuator-equipped knee ankle foot orthosis according to claim 1, wherein the thigh-side brace does not extend above the hip joint, and, wherein the thigh orientation detecting means is disposed below the hip joint of the user.

3. An actuator-equipped knee ankle foot orthosis comprising: a thigh-side brace to be attached to a user's thigh; a lower leg-side brace to be attached to the user's lower leg, the lower leg-side brace being connected to the thigh-side brace so as to be rotatable around the user's knee joint; an actuator unit attached to the thigh-side brace and capable of imparting assisting force around the user's knee joint to the lower leg-side brace; a thigh orientation detecting means capable of detecting an angle-related signal concerning a hip joint angle that is a forward and backward swing angle of the user's thigh, wherein the angle-related signal is not a direct measurement of the hip joint angle; and a control device configured to manage operational control for the actuator unit, wherein for each gait cycle, the control device calculates a thigh phase angle based on the angle-related signal and a drift elimination process, obtains an assisting force to be imparted to the lower leg-side brace by applying the thigh phase angle to an assisting force control data, which is stored in the control device in advance and indicates a relationship between the thigh phase angle and a size of the assisting force to be imparted to the lower leg-side brace, and controls the actuator unit to output the assisting force, wherein the gait cycle includes a heel contact phase including a heel contact time point when the user's heel contacts a surface in front of the user's body axis, a stance phase when the heel-contacted leg, after heel contact, is relatively moved backward while being in contact with the surface, and a swing phase when the leg contacting the surface since the end of the stance phase is raised and relatively moved forward, and wherein the assisting force control data is configured so that the actuator unit outputs no assisting force in a period after an initial stage of the swinging phase in which the actuator unit outputs the assisting force for rotating the lower leg-side brace in a knee bending direction around the user's knee joint to raise the user's leg, and wherein the control device inhibits an operation of the actuator unit in a case where a length of a vector defined by the hip joint angle and the hip joint angular velocity that has been used when calculating the thigh phase angle is between zero and the predetermined threshold value.

4. An actuator-equipped knee ankle foot orthosis comprising: a thigh-side brace to be attached to a user's thigh; a lower leg-side brace to be attached to the user's lower leg, the lower leg-side brace being connected to the thigh-side brace so as to be rotatable around the user's knee joint; an actuator unit attached to the thigh-side brace and capable of imparting assisting force around the user's knee joint to the lower leg-side brace; a thigh orientation detecting means capable of detecting an angle-related signal concerning a hip joint angle that is a forward and backward swing angle of the user's thigh, wherein the angle-related signal is not a direct measurement of the hip joint angle; and a control device configured to manage operational control for the actuator unit, wherein for each gait cycle, the control device calculates a thigh phase angle based on the angle-related signal and a drift elimination process, obtains an assisting force to be imparted to the lower leg-side brace by applying the thigh phase angle to an assisting force control data, which is stored in the control device in advance and indicates a relationship between the thigh phase angle and the size of the assisting force to be imparted to the lower leg-side brace, and controls the actuator unit to output the assisting force, wherein the gait cycle includes a heel contact phase including a heel contact time point when the user's heel contacts a surface in front of the user's body axis, a stance phase when the heel-contacted leg, after heel contact, is relatively moved backward while being in contact with the surface, and a swing phase when the leg contacting the surface since the end of the stance phase is raised and relatively moved forward, and wherein the assisting force control data is configured so that the actuator unit outputs the assisting force for rotating the lower leg-side brace in a knee extending direction around the user's knee joint in a later stage of the swing phase that is after an initial stage of the swinging swing phase in which the actuator unit outputs the assisting force for rotating the lower leg-side brace in a knee bending direction around the user's knee joint to raise the user's leg before the heel contact time point, and wherein the control device inhibits an operation of the actuator unit in a case where a length of a vector defined by the hip joint angle and the hip joint angular velocity that has been used when calculating the thigh phase angle is between zero and the predetermined threshold value.

* * * * *